(12) United States Patent
Arisz et al.

(10) Patent No.: US 8,709,390 B2
(45) Date of Patent: Apr. 29, 2014

(54) BLOCKY HYDROXYETHYLCELLULOSE, DERIVATIVES THEREOF, PROCESS OF MAKING AND USES THEREOF

(75) Inventors: Petrus Wilhelmus Franciscus Arisz, Amsterdam (NL); Kate M. Lusvardi, Chadds Ford, PA (US); Tuyen T. Nguyen, Newark, DE (US)

(73) Assignee: Hercules Incorporated, Wilmington, DE (US)

( * ) Notice: Subject to any disclaimer, the term of this patent is extended or adjusted under 35 U.S.C. 154(b) by 1428 days.

(21) Appl. No.: 11/353,621

(22) Filed: Feb. 14, 2006

(65) Prior Publication Data

US 2006/0182703 A1 Aug. 17, 2006

Related U.S. Application Data

(60) Provisional application No. 60/653,864, filed on Feb. 17, 2005.

(51) Int. Cl.
*A61K 8/73* (2006.01)
*A61Q 19/00* (2006.01)
*C04B 24/38* (2006.01)

(52) U.S. Cl.
CPC ........... *A61K 8/731* (2013.01); *A61Q 19/00* (2013.01); *C04B 24/383* (2013.01)
USPC .......... 424/70.13; 106/31.36; 536/95

(58) Field of Classification Search
CPC ....... A61K 8/731; A61Q 19/00; C04B 24/383
USPC .......... 424/70.13; 106/31.36; 536/95
See application file for complete search history.

(56) References Cited

U.S. PATENT DOCUMENTS

| | | | | |
|---|---|---|---|---|
| 2,572,039 A | 11/1949 | Klug et al. | ............ | 260/231 |
| 2,682,535 A | 11/1950 | Broderick | ............ | 260/231 |
| 2,744,894 A | 9/1952 | Benedict et al. | ............ | 260/231 |
| 3,131,176 A | 4/1964 | Klug | ............ | 260/231 |
| 3,131,177 A | 4/1964 | Klug et al. | ............ | 260/231 |
| 4,009,329 A | 2/1977 | Arney et al. | ............ | 536/84 |
| 4,084,060 A | 4/1978 | Glass, Jr. et al. | ............ | 536/96 |
| 4,228,277 A | 10/1980 | Landoll | ............ | 536/90 |
| 4,826,970 A | 5/1989 | Reid et al. | ............ | 536/66 |
| 4,904,772 A | 2/1990 | Sau | ............ | 536/90 |
| 2004/0151681 A1* | 8/2004 | Busk et al. | ............ | 424/70.13 |
| 2005/0139130 A1 | 6/2005 | Partain | ............ | 106/730 |

FOREIGN PATENT DOCUMENTS

| | | | | |
|---|---|---|---|---|
| CA | 1 014289 | 7/1977 | ............ | 400/16 |
| EP | 0 539 979 A2 | 5/1993 | ............ | 11/193 |
| EP | 1 858 970 | 8/2008 | | |
| GB | 1 368 705 | 10/1974 | ............ | 21/26 |
| WO | WO 03/106366 A1 | 12/2003 | ............ | 16/2 |

OTHER PUBLICATIONS

Wirick MG. Study of the Substitution Pattern of Hydroxyethylcellulose and Its Relationship to Enzymic Degradation. J Polymer Sci 6:1705-1718, 1968.*
Natrosol Hydroxyethylcellulose: A Nonionic Water-Soluble Polymer. Aqualon Product and Technical Information. Hercules Inc. 1999.*
F-G. Hanisch, Biological Mass Spectrometry, 23 (1994) p. 309-312.
B. Lindberg, u. Lindquist and O. Stenberg, Carbohydrate Research, 170 (1987) p. 207-214.
P. W. Arisz, J. A. Lomax and J. J. Boon, Carbohydrate Research, 243 (1993) 99-114.
Cellosize HMHEC 500, Nov. 2005, p. 1-6, The Dow Chemical Company.
Bermocoll, "Cellulose Ether," Akzo Nobel Brochure, CCD 2200, (2000), pp. 1-23, Stenungsund, Sweden.
Bermocoll EBM 5500, CCD 1404, Bermodol Bermocoll, (2004), p. 1.

* cited by examiner

*Primary Examiner* — Brandon Fetteroff
*Assistant Examiner* — Yih-Horng Shiao
(74) *Attorney, Agent, or Firm* — Shaorong Chen; Joanne Rossi; Michael Herman

(57) ABSTRACT

This invention relates to non-uniformly substituted ("blocky") hydroxyethylcelluloses (HECs) and derivatives thereof that exhibit associative behavior in both neat solutions and in filled systems. The HECs and derivatives thereof exhibit unique and highly desirable rheology and are more efficient in thickening aqueous systems than prior art HEC products. These blocky HECs can be distinguished from prior art and commercial HEC products by having an unsubstituted anhydroglucose trimer ratio (U3R) greater than 0.21 and the hydroxyethyl molar substitution greater than about 1.3 and less than about 5. This invention also relates to processes for making blocky HEC and uses thereof in functional systems.

35 Claims, 1 Drawing Sheet

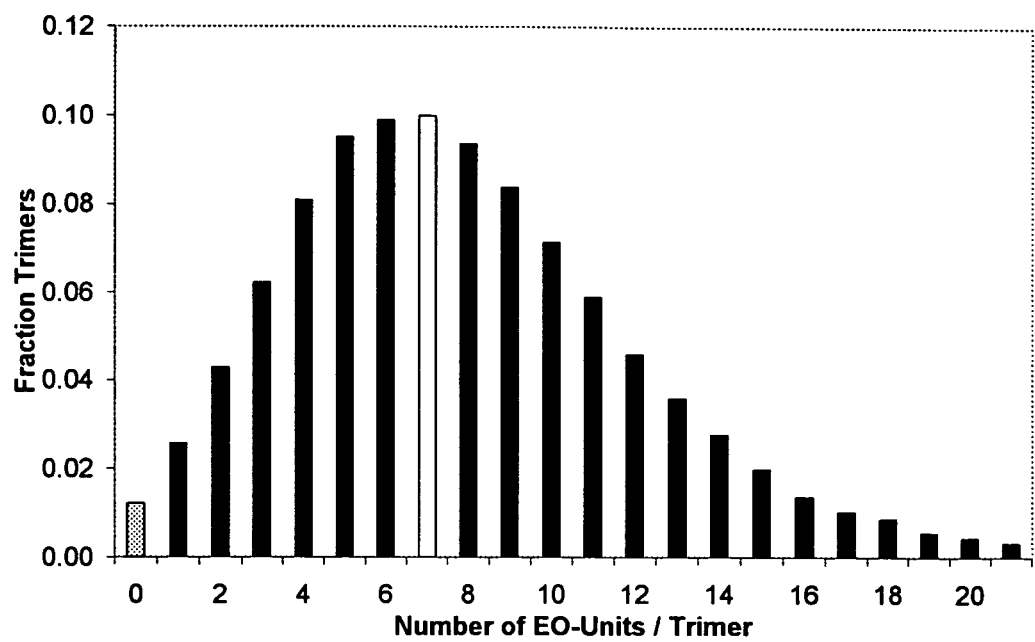

BLOCKY HYDROXYETHYLCELLULOSE, DERIVATIVES THEREOF, PROCESS OF MAKING AND USES THEREOF

This application claims the benefit of U.S. Provisional Application No. 60/653,864, filed Feb. 17, 2005.

FIELD OF INVENTION

The present invention relates to cellulose ether compositions, derivatives thereof, processes for making the composition and uses thereof in functional systems. More specifically, this invention relates to non-uniformly substituted ("blocky") hydroxyethylcelluloses (HECs) and derivatives thereof. This invention also relates to processes for making blocky HEC and uses thereof in functional systems.

BACKGROUND OF THE INVENTION

Hydroxyethylcellulose (HEC) is a cellulose ether usually made by reacting alkali cellulose with ethylene oxide (EO). In general, the molar ratio of EO to the anhydroglucose units of cellulose is higher than 1.5 to provide adequate water-solubility to the cellulose backbone. HEC is a water-soluble/water-swellable polymer that generally is used to viscosity aqueous media of functional systems such as personal care and household products, paints, construction material products, paper coatings, oilfield media, emulsions, latex components, etc. Furthermore, high molecular weight HEC is used in the pharmaceutical industry as an excipient to provide a swellable diffusion barrier in controlled release applications.

In commercial HECs that are made by a single-stage ethoxylation of cellulose, the hydroxyethylene substituents are nearly randomly distributed among the anhydroglucose segments of the polymer. Examples of prior art that disclose the preparation of HEC are U.S. Pat. Nos. 2,572,039, 2,682,535, 2,744,894, and 3,131,177. Another commercial HEC product is a more highly substituted HEC in which the ethylene oxide is reacted in two-steps thereby reducing the amount of unsubstituted anhydroglucose units. This results in the formation of a cellulose derivative that is less susceptible to enzymatic degradation, i.e., enhanced resistance to biodegradation. Examples of prior art that disclose the preparation of this type of HEC are U.S. Pat. No. 3,131,176, Canadian Patent 1014289, and U.S. Patent Application U.S. 2005/0139130 A1. The solution viscosities of HECs with these types of EO substitution patterns usually depend on the molecular weight of the cellulose backbone.

Furthermore, HECs can be modified with additional substituents to improve functionality. For example, U.S. Pat. No. 4,228,277 discloses the use of long chain alkyl modifiers having 10 to 24 carbon atoms. Another example of a modified HEC is disclosed in U.S. Pat. No. 4,826,970 that describes a carboxymethyl hydrophobically modified hydroxyethyl cellulose ether derivative (CMHMHEC) that is used as thickeners and protective colloids in water based protective coating compositions. U.S. Pat. No. 4,904,772 discloses a water-soluble HEC derivative that has a mixed hydrophobe having two or more hydrophobic radicals having 6 to 20 carbons whereby one of the hydrophobic radicals has a carbon chain length that is at least two carbon atoms longer than that of the other hydrophobic radical. U.S. Pat. No. 4,663,159 discloses a water-soluble, cationic hydroxyethyl cellulose.

Commercial HEC products are the thickeners of choice in many industries because they provide the desired rheology and thickening efficiency. Notwithstanding, a need still exists for an HEC-based rheology modifier that would be more efficient in thickening aqueous systems and interact more strongly with components in the system and/or with itself so that additional desired rheological properties can be achieved.

SUMMARY OF THE INVENTION

The present invention is related to "blocky" HEC products that have unique thickening efficiency in neat solutions and functional systems. In other words, the HECs of the instant invention show associative properties that are unknown in commercial HEC products. An advantage of this product is that it provides a much higher solution viscosity than regular commercial HEC at similar concentrations and molecular weight. Consequently, a lesser amount of the HEC of the present invention can produce comparable or better viscosity relative to analogous commercial HECs of similar molecular weight. The HECs and HEC derivatives of the present invention form solutions that have a high elasticity that is characteristic of a strongly associative polymer network as well as unique adsorption characteristics and interaction with media components. The gelling properties and suspending properties of the present invention are better than similar HEC products of the prior art.

The present invention is directed to HECs that have hydroxyethyl groups that are non-uniformly distributed on the cellulose backbone, wherein the ratio of unsubstituted anhydroglucose trimers to the most frequently occurring substituted anhydroglucose trimers (U3R) is greater than 0.21 and the hydroxyethyl molar substitution is greater than about 1.3 and less than about 5.0.

The present invention is further directed to a slurry process for making the above mentioned HEC composition comprising A) mixing and reacting cellulose, water and a base reagent in an organic solvent for a sufficient time and at a sufficient temperature in order to form a first base reagent cellulose mixture, wherein the water to anhydroglucose (AGU) molar ratio is in the range of about 5 to 35 and (a) the base reagent to AGU molar ratio is greater than about 1.6 or (b) the base reagent to AGU molar ratio is less than about 0.4

B) (i) when (a) is used from Step A, then sufficient acid is added in order to reduce the base reagent concentration to a base reagent to AGU molar ratio of no less than about 0.6 to form a second base reagent cellulose mixture, or (ii) when (b) is used from Step A, then sufficient ethylene oxide is added and reacted at a sufficient temperature and for a sufficient time to form a HEC product with a hydroxyethyl molar substitution of less than 1.3, followed by additional base reagent to adjust the base reagent to AGU molar ratio to greater than about 1.0 to form a base reagent HEC mixture, and C) then adding to the second base reagent cellulose mixture from B(i) or to the base reagent HEC cellulose mixture from B(ii) a sufficient amount of ethylene oxide and reacting at a sufficient temperature and for a sufficient time in order to form the final HEC composition.

The HEC product prepared by the above mentioned process can optionally be further reacted with at least one other derivatizing reagent to form a modified HEC product.

Likewise, the HEC or modified HEC product, optionally, can further be reacted with a viscosity reducing agent.

The present invention is also related to a functional system composition including the non-uniformly substituted HEC composition or derivatives thereof.

BRIEF DESCRIPTION OF THE DRAWING

FIG. 1 shows a bar graph of the ethylene oxide distribution profile of a HEC polymer.

DETAILED DESCRIPTION OF THE INVENTION

It has been surprisingly found that a HEC or derivatives thereof having a non-uniformly or blocky substitution pattern can produce unique rheology that has not been noted prior to this invention.

The present invention is directed to blocky HECs and modified HECs (nonionic, anionic, and cationic) in which a large fraction of the anhydroglucose units (AGU) in the cellulose backbone are not substituted with ethylene oxide (EO). Upon degradation, these unsubstituted anhydroglucose units exist as monomers and oligomers. The characteristic that makes these blocky HECs unique is an unsubstituted trimer ratio (U3R) that is greater than 0.21, preferably greater than 0.235, and a hydroxyethyl molar substitution that is greater than about 1.3 and less than about 5.0. This unique class of HECs shows associative behavior through hydrogen bonding and exhibits significantly higher solution viscosities as compared to other classes of HECs with similar hydroxyethyl molar substitution (HE MS) and cellulose molecular weight. Furthermore, this non-uniformly substituted HEC provides a unique template for reacting hydrophobes that are concentrated in the EO-rich regions in a non-uniform manner to achieve novel rheological properties. Post addition of non-ionic or ionic substituents may be necessary to improve water-solubility or functionality.

In accordance with the present invention, the blocky HEC composition can be further modified with one or more non-ionic, anionic, and cationic substituents or mixtures thereof. The substituents are attached to the HEC backbone via an ether, ester, or urethane linkage.

When the substituents have nonionic chemical functionality, the substituents have the formula:

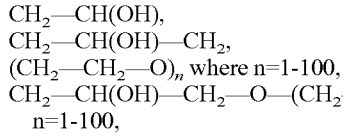

CH$_2$—CH(OH),
CH$_2$—CH(OH)—CH$_2$,
(CH$_2$—CH$_2$—O)$_n$ where n=1-100,
CH$_2$—CH(OH)—CH$_2$—O—(CH$_2$—CH$_2$—O)$_n$ where n=1-100,
CH(R)—C(O)—CH$_2$, and
R is selected from one of the following groups:

i) an acyclic or cyclic, saturated or unsaturated, branched or linear hydrocarbon moiety having 1 to 30 carbon atoms, ii) an acyclic or cyclic, saturated or unsaturated, branched or linear heterohydrocarbon moiety having 1 to 30 carbon atoms and one of more oxygen, nitrogen, or silicone atoms, iii) an acyclic or cyclic, saturated or unsaturated, branched or linear hydrocarbon moiety having 1 to 30 carbon atoms and one or more aromatic hydrocarbon groups, iv) an acyclic or cyclic, saturated or unsaturated, branched or linear heterohydrocarbon moiety having 1 to 30 carbon atoms and one or more oxygen, nitrogen, or silicone atoms and one or more aromatic groups, and v) an acyclic or cyclic, saturated or unsaturated, branched or linear, heterohydrocarbon moiety having 1 to 30 carbon atoms and one or more oxygen, nitrogen, or silicone atoms and one or more heteroaromatic groups containing one or more oxygen, nitrogen, or silicone groups.

Based on the formula R above, the substituents may be selected from alkyl, alkenyl, alkynyl, aryl, alkyl aryl, aryl alkyl, alkenyl aryl, aryl alkenyl, or mixtures thereof having, when possible, from 1 to 30 carbon atoms.

When the substituents have anionic chemical functionality, the anionic chemical functionality can be carboxylate, sulfate, sulfonate, phosphate, phosphonate or mixtures thereof. More specific examples of this functionality are carboxymethyl, sulfoethyl, phosphonomethyl, and mixtures thereof.

When the substituents have cationic chemical functionality, the substituents have the formula R$^1$R$^2$R$^3$R$^4$N$^+$ (A$^-$), where R$^1$ is
—CH$_2$—CHOH—CH$_2$— or —CH$_2$—CH$_2$—, and R$^2$, R$^3$, R$^4$ are each independently selected from an alkyl or aryl alkyl group having 1 to 20 carbon atoms, and A$^-$ is a halide, sulfate, phosphate, or tetrafluoroborate ion.

More specifically, the cationic substituents can be selected from 2-hydroxpropyltrimethylammonium chloride, 2-hydroxypropyldodecyldimethylammonium chloride, 2-hydroxypropylcocoalkyldimethylammonium chloride, 2-hydroxypropyloctadecyldimethylammonium chloride and mixtures thereof.

Another important cationic group that can be used in this invention is the group derived from the grafting reaction of diallyldimethylammonium chloride with HEC or its derivatives.

In accordance with the present invention, more specific modified hydroxyethylcellulose examples are methyl hydroxyethylcellulose, ethyl hydroxyethylcellulose, octyl hydroxyethylcellulose, cetyl hydroxyethylcellullose, cetoxy-2-hydroxypropyl hydroxyethylcellulose, butoxy-2-hydroxypropyl hydroxyethylcellulose, butoxy-2-hydroxypropyl cetyl hydroxyethylcellulose, butoxy-2-hydroxypropyl cetoxy-2-hydroxyethylcellulose, carboxymethyl hydroxyethylcellulose, carboxymethyl ethyl hydroxyethylcellulose, carboxymethyl octyl hydroxyethylcellulose, carboxymethyl cetyl hydroxyethylcellulose, carboxymethyl cetoxy-2-hydroxypropylcellulose, carboxymethyl butoxy-2-hydroxyethylcellulose, sulfoethyl hydroxyethylcellulose, sulfoethyl ethyl hydroxyethylcellulose, sulfoethyl cetyl hydroxyethylcellulose, sulfoethyl cetoxy-2-hydroxypropylcellulose, 2-hydroxypropyltrimethylammonium chloride hydroxyethylcellulose, 2-hydroxypropyltrimethylammonium chloride ethyl hydroxyethylcellulose, 2-hydroxypropyltrimethylammonium chloride butoxy-2-hydroxypropyl hydroxyethylcellulose, 2-hydroxypropyltrimethylammonium chloride octyl hydroxyethylcellulose, 2-hydroxypropyltrimethylammonium chloride cetyl hydroxyethylcellulose, 2-hydroxypropyltrimethylammonium chloride cetoxy-2-hydroxypropyl hydroxyethylcellulose, 2-hydroxypropyllauryldimethylammonium chloride hydroxyethylcellulose, 2-hydroxypropyltrimethylammonium chloride 2-hydroxypropyllauryidimethylammonium chloride hydroxyethylcellulose, diallyldimethylammonium chloride grafted hydroxyethylcellulose, and diallyldimethylammonium chloride grafted cetyl hydroxyethylcellulose.

In accordance with the present invention, the preferred process for making a non-uniformly substituted HEC product requires a two-step alkalization of the cellulose, while only a single-stage hydroxyethylation is necessary. This differs from the two-step hydroxyethylation that has been described in prior art to improve the enzyme resistance of HECs. The initial alkalization step is performed at an alkali to AGU molar ratio higher than 1.6 and at a water to AGU molar ratio in the range of about 5 to 35. Next, the alkali cellulose is neutralized with an acid to an alkali to AGU molar ratio greater than 0.6, preferably between 1.2 and 1.0. The alkali neutralization step may be done as a single addition, multiple additions, or a continuous addition of the neutralizing aid, with or without the presence of ethylene oxide. Upon completion of the hydroxyethylation, the product can be viscosity reduced, purified, dried, and ground as known to those skilled in the art.

Also, in accordance with the present invention, non-uniformly substituted HEC can be produced using a "reverse" two-step alkalization process as herein described. In this case, the cellulose is partly alkalized at a caustic to AGU molar ratio that is insufficient to open up the cellulose fibers. Typical alkali to AGU molar ratios are between 0.2 and 0.4 and water to AGU molar ratios are in the range of about 5 to 35. The cellulose is first hydroxyethylated to less than 1.3 at this stage before more alkali is added in the second stage to reach alkali to AGU molar ratios between 1.0 to 2.0, preferably between 1.0 and 1.4. After sufficient time, the intermediate HEC is further hydroxyethylated to achieve the final HE MS.

In the slurry process of the present invention, organic solvent used in this process is selected from ethanol, isopropanol, tert-butanol, acetone, methyl ethyl ketone, dimethoxyethane, and mixtures thereof. This slurry process uses alkalis that are selected from lithium hydroxide, sodium hydroxide, potassium hydroxide, and mixtures thereof. The raw cellulose starting material used in the process for making the blocky HECs can be cotton linters, wood pulps or mixtures thereof.

The blocky HEC compositions mentioned above can be optionally further reacted with at least another derivatizing reagent to form a modified hydroxyethylcellulose composition. The derivatizing reagent used to make this modified hydroxyethylcellulose composition can be nonionic, cationic, or anionic organic compounds or mixtures thereof. These organic compounds capable of reacting with the hydroxyls groups of the HEC can be halides, epoxides, glycidyl ethers, carboxylic acids, isocyanates, or mixtures thereof.

The blocky HEC or derivatives thereof made by the slurry processes mentioned above can be further reacted with a viscosity reducing agent, such as peroxide, persulfate, peracid, salt of halide oxo acids, oxygen, or ozone. This enables a person using this process to modify the final product to the desired viscosity or other properties for the desired end use.

The process and process conditions determine how the EO is distributed along the cellulose backbone. Products of the invention are characterized and can be differentiated from HECs made by prior art by reducing the polymer down to monomers and oligomers and measuring the degree of unsubstituted oligomers, more specifically unsubstituted trimers. A novel parameter called the unsubstituted trimer ratio (U3R) can be defined as the ratio of the molar fraction of unsubstituted trimers to the molar fraction of the most abundant class of (hydroxyethyl-substituted) trimers, with $0 \leq U3R \leq 1.0$. U3R is measured by a mass spectrometric technique that is described below. The U3R of the HECs of present invention are equal to or more than about 0.21, preferably greater than 0.235.

Trimers, oligomers with a degree of polymerization (DP) of 3 anhydroglucose units, and other compounds of structure 1 are made by partial methanolysis of permethylated HEC derivatives. It is assumed that the cleavage of the permethylated HEC-backbone is a random process and that the formed oligomers of structure 1 have an EO-distribution that is representative for the EO-distribution of the whole sample.

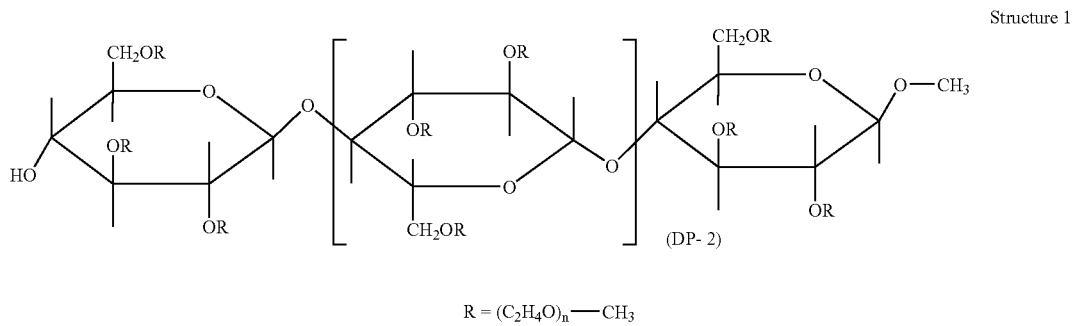

Structure 1

$R = (C_2H_4O)_n\text{—}CH_3$

In general, permethylated derivatives of HEC polymers can be prepared by the methylation reaction that is applied in the methylation analysis procedure for polysaccharides. (See publications of F.-G. Hanisch, Biological Mass Spectrometry, 23 (1994) 309-312; B. Lindberg, U. Lindquist and O. Stenberg, Carbohydrate Research, 170 (1987) 207-214; and P. W. Arisz, J. A. Lomax, and J. J. Boon, Carbohydrate Research, 243 (1993) 99-114.)

Unsubstituted Trimer Ratio (U3R) Determination

More specifically, in the present invention, the investigated HEC polymers are dissolved or swollen in dimethyl sulphoxide (DMSO). The hydroxyl groups in the polymer are deprotonated using a lithium methylsulphinyl carbanion solution in DMSO and they are converted to methoxyl groups by the reaction with methyl iodide.

The obtained permethylated HEC polymer is purified. More specifically, the permethylated HEC polymer is extracted in three extraction steps with chloroform from an aqueous DMSO layer that is acidified to pH<2 with hydrochloric acid. The pooled chloroform extracts are washed four times with water. Some methanol is added after the last wash step and all solvents are evaporated.

The permethylated polymer is partially degraded by methanolysis. More specifically, the permethylated polymer is dissolved/swollen in methanol. Sufficient hydrochloric acid in methanol is added to get a hydrochloric acid concentration of about 0.50 molar. The sample is dissolved completely at 50° C. for 15 minutes. Partial methanolysis is done at 70° C. for 2.5 hours. The reaction is quenched by the addition of 2-methyl-2-propanol and all solvents are evaporated, yielding a residue that is composed of a mixture of oligomers of structure 1.

The residue is dissolved in methanol and a fraction of this sample is mixed with 2,5-dihydroxybenzoic acid solution that is spiked with sodium iodide. Mass spectra of the oligomer mixture are recorded with a Bruker Reflex II MALDI-TOF-MS (matrix assisted laser desorption ionization—time of flight—mass spectrometer), which instrument is equipped with a microchannel plate detector. The compounds 1 are measured as their sodium ion adducts. The mass numbers of the monoisotopic mass peaks of the trimers are m/z 667.32, 711.34, 755.35, 799.39, etc. It is assumed that all trimers are measured with equal probability, independent of their molar HE-substitution, chain length of the substituents and their positions in the anhydroglucose residues.

Trimer fractions are derived by two data processing steps from the measured peak intensities of their monoisotopic mass peaks. First the background signal of the MALDI spectrum is subtracted from the measured peak intensities. Secondly, mainly due to $^{13}$C-isotopes that are incorporated in structure 1 the monoisotopic mass peaks make up only 70.6, 68.9, 67.2, 65.6%, etc of all isotopes of trimers having 0, 1, 2, 3, etc attached EO-units, respectively. Unfortunately, the peak intensities of $^{13}$C-isotopes can not be measured accurately by MALDI-TOF-MS because of the recovery time that is needed for the microchannel plate detector after an intense mass peak has been recorded. In order to compensate the signal for the missing contribution of $^{13}$C-isotope peaks, the background corrected monoisotopic mass peak intensities are multiplied by a correction factor that is calculated from the theoretical isotope composition of the trimers. This factor increases with increasing number of C-atoms in 1, and values have been used of 1.417, 1.452, 1.488, 1.525, etc for trimers having 0, 1, 2, 3, etc attached EO-units, respectively.

FIG. 1 shows an example of the EO-distribution profile of trimers that are derived from a HEC polymer. The fraction of unsubstituted trimers is indicated in gray. The most abundant class of trimers in this example is that of trimers with 7 attached EO-units. This class is indicated in white. The unsubstituted trimer ratio, i.e. the gray fraction divided by the white fraction, is calculated to be 0.121 for this example. It should be noted that the number of EO-units in the most abundant class of trimers varies, depending on factors as the molar substitution of the HEC and the process type by which the HEC was made, for example.

HEC derivatives that contain secondary substituents such as nonionic, cationic and anionic substituents and mixtures thereof are analyzed similarly as non-modified HECs. In the case of modification levels smaller than 3.5 substituents per 100 monomer units, such as associative hydrophobic reagents for example, less than 10% of the trimers are modified and consequently the fraction of modified trimers can be neglected.

The fraction of unmodified trimers decreases with increasing degree of substitution (DS) of the modifying agent. If the secondary substituent distribution is at random along the cellulose backbone, than only half of the trimers would remain unmodified at a DS level of 0.21. The carboxymethyl (CM)-modified HMHECs listed in Tables 2a, 3a and 4a all have CM-DS values in this order of magnitude and it is concluded for these samples that the fraction of CM-modified trimers cannot be neglected.

Furthermore, CM-groups that are attached to the HEC-backbone are converted into their methylesters by the derivatization procedure. The sodium ion adduct of dimers with two attached EO units and two attached CM-groups has m/z 667.28. The mass resolution of MALDI-TOF-MS is insufficient to separate this mass peak from m/z 667.32, i.e. the mass peak of unsubstituted trimers, so that an accurate U3R-value for carboxymethylated HEC-derivatives is not applicable (N/A).

Applications:

Many of these HEC samples exhibit novel and highly desirable rheology and performance properties in end use systems.

In accordance with the present invention, the viscosity builds up not only by means conventional to HEC, but also is boosted significantly by molecular association. The association leads to network formation and gel-like rheological properties in water and aqueous based functional systems that are shear reversible. The HECs and derivatives of the present invention have been shown to lower the HEC use-level needed and to provide unique rheological attributes as compared to commercial HECs available today.

Furthermore, these HECs and derivatives thereof may be used in applications where there is a need for a specific rheology characteristic, e.g., viscosity, thixotropy, yield stress, elasticity, or solid state characteristics such as thermoplasticity and film flexibility. Examples of functional systems includes aqueous based coatings (e.g., latex paints), building and construction materials (e.g., cements, plasters), personal care products (e.g., skin care, hair care, oral care, nail care, and personal hygiene products), household care products (e.g., industrial cleaning liquids, pet care products), pharmaceuticals (e.g., excipients for tablets, capsules, and granules), oilfield applications (e.g., drilling fluids, completion fluids, and fracturing fluids), civil engineering, printing inks, adhesives, paper coating formulations, and retention and drainage aids in paper making.

In accordance with the present invention, the functional system can either be prepared in a continuous or batch process and either in a stepwise addition of the ingredients or a simple mixing of all of the ingredients at once. The order of addition of the ingredients can also vary over a wide range of additions. For example, the functional ingredients can be individually added one at a time to the formulation or all at once or the blocky HEC products can be added directly to the formulated ingredients in a single step. Hence, the process of thickening an aqueous based functional system (e.g., personal care products, household care products, oil field servicing fluids, civil engineering servicing fluids, paper coating products, paper making compositions, building and construction fluids, mineral processing products, and water based protective coatings such as architectural and industrial coatings), includes adding and mixing a sufficient amount of the blocky HEC polymer of the present invention that is compatible with the aqueous based functional system to thicken the functional system. The resulting functional system has comparable or better rheology and viscosity properties as compared to when using similar thickening agents including commercial HECs.

Personal Care

In accordance with the present invention, when the composition is a personal care composition, it includes (a) from about 0.1% to about 99.0% by weight of the vehicle component and (b) at least one active personal care ingredient.

In accordance with the present invention, the personal care active ingredient must provide some benefit to the user's body. Personal care products include hair care, skin care, oral care, nail care, and personal hygiene products. Examples of substances that may suitably be included in the personal care products according to the present invention are as follows:

1) Perfumes, which give rise to an olfactory response in the form of a fragrance and deodorant perfumes which in addition to providing a fragrance response can also reduce body malodor;
2) Skin coolants, such as menthol, methyl acetate, methyl pyrrolidone carboxylate N-ethyl-p-menthane-3-carboxamide and other derivatives of menthol, which give rise to a tactile response in the form of a cooling sensation on the skin;
3) Emollients, such as isopropyl myristate, silicone oils, mineral oils and vegetable oils which give rise to a tactile response in the form of an increase in skin lubricity;

4) Deodorants other than perfumes, whose function is to reduce the level of or eliminate micro flora at the skin surface, especially those responsible for the development of body malodor. Precursors of deodorants other than perfume can also be used;

5) Antiperspirant actives, whose function is to reduce or eliminate the appearance of perspiration at the skin surface;

6) Moisturizing agents that keep the skin moist by either adding moisture or preventing moisture from evaporating from the skin;

7) Cleansing agents that remove dirt and oil from the skin;

8) Sunscreen active ingredients that protect the skin and hair from UV and other harmful light rays from the sun. In accordance with this invention a therapeutically effective amount will normally be from 0.01 to 10% by weight, preferably 0.1 to 5% by weight of the composition;

9) Hair treatment agents that condition the hair, cleans the hair, detangles hair, act as styling agents, volumizing and gloss agents, anti-dandruff agent, hair growth promoters, hair dyes and pigments, hair perfumes, hair relaxer, hair bleaching agent, hair moisturizer, hair oil treatment agent, and anti-frizzing agent;

10) Shaving products, such as creams, gels and lotions and razor blade lubricating strips;

11) Tissue paper products, such as moisturizing or cleansing tissues;

12) Beauty aids, such as foundation powders, lipsticks, and eye care; and

13) Textile products, such as moisturizing or cleansing wipes.

In personal care compositions, the rheology modifiers of the present invention can be used either alone or may also be used in combination with other known rheology modifiers including, but not limited to, polysaccharides (e.g., carrageenan, pectin, alginate), cellulose ethers, biopolymers (e.g., xanthan gum), synthetic polymers, and abrasive/thickening silicas.

Household Care

In accordance with the present invention, when the composition is a household care composition, it includes (a) from about 0.1% to about 99.0% by weight of the vehicle component and (b) at least one active household care ingredient.

In accordance with the present invention, the household care active ingredient must provide some benefit to the user. Household care products include fabric care, laundry detergent, hard surface cleaner, industrial institutional liquid soaps, and dish detergents. Examples of active ingredients or substances that may suitably be included according to the present invention are as follows:

1) Perfumes, that give rise to an olfactory response in the form of a fragrance and deodorant perfumes that in addition to providing a fragrance response can also reduce odor;

2) Insect repellent agent whose function is to keep insects from a particular area or attacking skin;

3) Bubble generating agent, such as surfactants which generates foam or lather;

4) Pet deodorizer such as pyrethrins that reduce pet odor;

5) Pet shampoo agents and actives, whose function is to remove dirt, foreign material and germs from the skin and hair surfaces;

6) Industrial grade bar, shower gel, and liquid soap actives that remove germs, dirt, grease and oil from skin, sanitize skin, and condition the skin;

7) All purpose cleaning agents that remove dirt, oil, grease, and germs from the surfaces in areas such as kitchens, bathroom, and public facilities;

8) Disinfecting ingredients that kill or prevent growth of germs in a house or public facility;

9) Rug and Upholstery cleaning actives that lift and remove dirt and foreign particles from the surfaces and also deliver softening and perfumes;

10) Laundry softener actives that reduce static and makes fabric feel softer;

11) Laundry detergent ingredients that remove dirt, oil, grease, and stains and kill germs;

12) Dishwashing detergents that remove stains, food, germs;

13) Toilet bowl cleaning agents that remove stains, kill germs, and deodorize;

14) Laundry prespotter actives that help in removing stains from clothes;

15) Fabric sizing agents that enhance appearance of the fabric;

16) Vehicle cleaning actives that remove dirt, grease, etc. from vehicles and equipment;

17) Lubricating agents that reduce friction between parts; and

18) Textile products, such as dusting or disinfecting wipes.

In household care compositions, the rheology modifiers of the present invention can be used either alone or may also be used in combination with other known rheology modifiers including, but not limited to, polysaccharides (e.g., carrageenan, pectin, alginate), cellulose ethers, biopolymers (e.g., xanthan gum), synthetic polymers, and abrasive/thickening silicas.

The above are only limited examples of personal care and household active ingredients and are not a complete list of active ingredients that can be used. Other ingredients that are used in these types of products are well known in the industry. In addition to the above ingredients conventionally used, the composition according to the present invention can optionally also include ingredients such as colorants, preservatives, antioxidants, nutritional supplements, activity enhancers, emulsifiers, viscosifying agents (such as salts, e.g., sodium chloride, ammonium chloride and potassium chloride), water-soluble polymers (e.g., HEC, modified HEC, carboxymethylcellulose), and fatty alcohols (e.g., cetyl alcohol), alcohols having 1-6 carbons, and fats and oils.

Protective Coatings

Water-based protective coating compositions (commonly referred to as paints) in which cellulose ether derivatives are commonly used include latex paints or dispersion paints, of which the principal ingredient is the film-forming binders that include latices such as styrene-butadiene copolymers, vinyl acetate homopolymers and copolymers, and acrylic homopolymers and copolymers. Other binders that are typically used in paints include alkyd resins, and epoxy resins. Typically, paints also contain opacifying pigments, dispersing agents and water-soluble protective colloids, the proportions being, by weight of the total composition, about 10 parts to about 50 parts of a latex, about 10 parts to about 50 parts of an opacifying pigment, about 0.1 part to about 2 parts of a dispersing agent, and about 0.1 part to about 2 parts of a water-soluble protective colloid. These protective coatings can be either aqueous based architectural or industrial coating compositions. Architectural coatings are intended for on-site application to interior or exterior surfaces of residential, commercial, institutional or industrial buildings. Industrial coatings are applied to factory-made articles before or after fabrication, usually with the aid of special techniques for application and drying.

Water-soluble polymers conventionally used in the manufacture of latex paints include casein, methyl cellulose, hydroxyethylcellulose (HEC), sodium carboxymethyl cellulose (CMC), polyvinyl alcohol, starch, and sodium polyacrylate. The HECs of the present invention can be used as rheology modifiers for water-based protective coating compositions.

Paper Coatings and Paper Making

Paper coating is a process in which the surface structure of paper or board is improved by applying a mineral coating that is subsequently dried. Coating process is the application of a water-borne pigment slurry, which is bound at the surface by one of several binders. Other coating components can be added to obtain a suitable rheology, and to impart properties such as brightness or water resistance.

A coating process can generally be divided into three different phases: (1) preparation of the coating formulation (known as called coating color), (2) coating and (3) drying. The general principles of formulating paper coating are mostly well known. Moreover, each paper maker has his own tailor-made recipes for his specific requirements. Therefore, it would not be possible to give a "recipe" for a specific coating process, coating type or printing process. However, a generic coating formulation recipe contains 75-90% pigment (such as clay, satin white, calcium carbonate, titanium dioxide, talc, aluminum hydroxide, calcium sulfate, barium sulfate, synthetics, etc.), 0.10-0.50% dispersant, 0.05-0.30% alkali, 5-20% binders (such as styrene-butadiene latices, acrylics, polyvinyl acetate, starch and starch derivatives, proteins such as casein, soya) and 0-2% co-binder (cellulose ethers, polyvinyl alcohol and solution or polyacrylates emulsion). Other functional additives such as lubricants, optical brightening agents and defoamers are often added to the coating formulation. All amounts of ingredients are based on weight of pigment. The HECs of the present invention can be used as rheology modifiers for water-borne paper coating compositions.

In addition to paper coating, the blocky HECs of the present invention can be used in papermaking process and for surface sizing. In papermaking process, the blocky HEC can be used as an additive in the stock as a refining agent, wet-strength agent, dry strength agent, internal bonding agent, water retention agent and improving the sheet formation. For surface sizing, the blocky HEC can be used as a binding agent and aiding in film formation.

Oilfield Servicing Fluids

Drilling an oil or gas well is a complex operation, involving several steps before and after the well is put into production. Primary oil-recovery operations include drilling the well, cementing the casing to the formation and completing the well prior to oil or gas production. Workover operations may be necessary during remedial work in producing wells, usually as an attempt to enhance or prolong the economic life of the well. When the flow rate of the fluid is diminished, the reservoir may be treated in some manner to increase the flow of fluid into the wellbore. This operation is called secondary recovery, known as fracturing/stimulation operations. They are performed either by acid wash or hydraulic fracturing. When the reservoir is depleted, enhanced oil recovery operations may be needed to increase the production rate. This operation is called tertiary recovery, and involves injection of fluids into the formation surrounding the production well to increase the flow rate of the formation fluid into the wellbore.

Drilling fluids are an integral element of the drilling program for primary oil recovery. They are especially designed to perform numerous functions that condition the success of drilling operations. Their principal functions include, but not limited to, are:

An effective hole cleaning efficiency (H.C.E.).
Maintaining the stability of the open hole-formation.
Formation of a thin and low-permeability filter cake on the formation.
Minimizing formation damage.
Friction reduction between the drilling string and the formation.
Cool and clean the drill bit.

To perform these functions, drilling fluids should possess particular properties with regard to rheology, density, and filtration control. Filtration control is a key performance attribute that affects all other properties. In fact, loss of significant amount of water from the drilling fluid into the formation would result in irreversible change of the overall drilling fluid properties (density and rheology) that would seriously affect the stability of the borehole.

Among a variety of additives, carboxymethyl cellulose (CMC), HEC and polyanionic cellulose (PAC) are widely used to optimize water-based drilling fluid properties. High-viscosity types are used for rheology and fluid loss control properties while low viscosity types are exclusively used for filtration control properties. In most cases, these types are used together in a drilling fluid composition. During drilling operations, optimum drilling fluid attributes are further achieved by combining different components including clay, CMC/PAC, xanthan gum (primary rheology modifier), starches (improved filtration control) and other synthetics polymers that may be required for dispersing or shale inhibition properties.

Completion and workover fluids are specialized fluids used during well completion operations and remedial workover procedures. They are placed across the chosen pay zone after the well has been drilled but prior to putting it on production. These fluids must control not only subsurface pressure with density, but also must minimize formation damage during completion and workover operations to improve oil or gas production rate. Because all wells are susceptible to formation damage to some degree (from a slight reduction in the production rate to complete plugging of specific zones) and the potential for permanent damage is greater during completion and workover operations than it is during drilling, it is imperative to use a fluid that causes the least possible damage to the pay zone formation. The principal functions of completion and workover fluids include, but not limited to, are:

Control subsurface pressures.
Minimize formation damage.
Maintain well bore stability.
Control fluid losses to the formation.
Transport solids.
Maintain stable fluid properties.

The types of completion and workover fluids can be categorized into clear solids-free brines, polymer viscosified brines with bridging/weighting agents, and other fluids including oil base, water base, converted muds, foam, etc. The primary selection criteria for an appropriate completion or workover fluid are density. Clear, solids free brines are the most commonly used fluids and are viscosified with polymers (CMC/PAC, xanthan gum, guar and guar derivatives, and HEC) and may incorporate solids that can be dissolved later, such as acid soluble calcium carbonate or sized sodium chloride salt, for increased density or bridging purposes. While HEC is the most suitable polymer for brine based systems, CMC/PAC and xanthan gum find their use in low density (up to 12 ppg) monovalent salts based brines.

Hydraulic fracturing may be defined as the process in which fluid pressure is applied to the exposed reservoir rock until failure or fracturing occurs. After failure of the rock, a sustained application of fluid pressure extends the fracture outward from the point of failure. This may connect existing natural fractures as well as provide additional drainage area from the reservoir. The fluid used to transmit the hydraulic pressure to the reservoir rock is called the fracturing fluid. To prevent the fracture from dosing when pumping is stopped, propping agents, such as sized sand, are added to the fracturing fluid. The propping agent acts as supports to hold the fracture open after the treatment and to provide an improved ability of the fracture to conduct oil or gas through the fracture to the wellbore.

The blocky HECs and derivatives thereof of the present invention can be used as rheology modifiers for aqueous based oilfield servicing fluids with improved efficiency.

Civil Engineering Servicing Fluids

Civil engineering applications include tunneling, diaphragm walling, pilling, trenching, horizontal drilling, and water-well drilling. These applications are often characterized by their closeness to agglomerations where strict environmental regulation is in effect to minimize any kind of pollution or contamination. The corresponding working sites are further characterized by the availability of very poor mixing equipment on-site to efficiently disperse and dissolve the water-soluble polymers (WSPs). There is a desire in civil engineering applications for polymer suspensions that are stable, environmentally friendly, and meet all discharge regulations.

The blocky HEC and derivatives thereof of the present invention are used as rheology modifiers in fluids for civil engineering applications including tunneling, piling, diaphragm walling, drilling, and bentonite doping.

Construction/Building Compositions

Building compositions, also known as construction materials, include concrete, tile cement and adhesives, projection plasters, stuccos based on cement and synthetic binders, ready mixed mortars, manually applied mortars, underwater concrete, joint cement, joint compounds, gypsum board, crack fillers, floor screeds, and adhesive mortars. These compositions are essentially Portland cements, Plaster of Paris or vinyl copolymers containing functional additives to impart characteristics required for various construction applications. The joint cement can contain clay and mica or can be clay free (i.e., contain less than 0.5 wt % clay). While lime was once the preferred material for controlling the water ratio in the building compositions, cellulose ethers are at present time the most used because of their contribution to improve the water retention characteristics and other physical properties such as workability, consistency, open time, tack, bleeding, adhesion, set time, and air entrainment.

The blocky HEC and derivatives thereof of the present invention are used as rheology modifiers in the above mentioned construction and building material compositions.

Pharmaceuticals

Pharmaceutical compositions normally are in the form of tablets, capsules, or granules. The sole purpose of a pharmaceutical composition, regardless of its form, is to deliver a therapeutically active medicament to the desired place of use. The most common form of the medicament delivery system is the tablet form. In the tablet or capsule form, it is common practice to use at least one inert ingredient for production, delivery, and economic considerations. Examples of inert ingredients are excipients, diluents, fillers, and binders. The combination of the medicament with the inert ingredients provides a formulation that can be directly compressed into tablets or made into granules or agglomerations for encapsulation. In order to provide a directly compressible product, these excipients must have certain physical properties, including flow ability, sufficient particle size distribution, binding ability, acceptable bulk and tap densities, and acceptable dissolution properties in order to release the medicament upon oral administration.

The blocky HECs or derivatives thereof of the present invention can be used in free flowing, directly compressible slow release granule compositions that can be prepared by dry-blending, roller-compaction, or wet-agglomeration for use as a pharmaceutical excipient. This excipient contains from about 5 to about 80% by weight of the blocky HEC or HEC derivative. This excipient can also contain an inert pharmaceutical filler in the amount of from about 0.01 to about 95% by weight. Examples of the pharmaceutical fillers are monosaccharides, disaccharides, polysaccharides, polyhydric alcohols, inorganic compounds, and mixtures thereof. This excipient composition can also contain from about 0.01 to 50% of an additional control release agent such as cellulose ethers, cellulose esters, polyethylene oxides, polyvinyl alcohol and copolymers, methacrylic acid derivatives, waxy-fatty materials, natural hydrocolloids, and Carbopol® derivatives.

In accordance with the present invention, a control release pharmaceutical tablet for oral administration is composed of from about 5 to about 80% by weight of the total composition of the blocky HEC or derivatives thereof, up to about 90% by weight of an inert pharmaceutical filler (as mentioned above), and an effective amount of a therapeutically active medicament to render a therapeutic effect. The ratio of medicament to the blocky HEC (hydrophilic material) is based in part upon the relative solubility of the medicament and the desired rate of release. By varying this ratio and/or the total weight of the tablet, one can achieve different slow release profiles, and may extend the dissolution of some medicaments to about 24 hours.

An immediate release tablet composition of the present invention is composed of from about 0.5 to 10% by weight of the blocky HEC, suitable fillers and tableting aids, and an effective amount of a therapeutically active medicament. The amount of the active medicament depends on the desired amount needed to deliver the desired effect.

EXAMPLES

The following Examples indicate various possible methods for making, describing, and using the HECs of the present invention. These Examples are merely illustrative, and are not to be construed as limiting the present invention to particular compounds, processes, conditions, or applications. All parts and percentages are by weight unless otherwise stated.

The following processes are used to prepare the Examples and Comparative Examples that are designated in the various Tables. Table 1 shows the description of the individual Examples.

Procedures for Preparing Samples:

Process A

Cellulose, water, and solvents were charged to a nitrogen-sparged, high pressure reaction kettle per the ratios described in the various tables. The reactor was inerted with nitrogen and pressure tested. The caustic was added and the alkali cellulose slurry temperature was maintained at 20° C. for approximately 1 hour. Ethylene oxide was added and the temperature was raised to 45° C. and maintained for 45 minutes. The temperature was then raised to 100° C. and held for 60 minutes to complete the reaction. The reaction mixture was cooled down to ambient temperature and neutralized with sufficient acid. The product was then purified and ground to the desired particle size.

Process B

Cellulose, water, and solvent were charged to a nitrogen-sparged, high pressure reaction kettle per the ratios described in the various tables. The reactor was inerted and pressure tested. The caustic was added and the alkali cellulose slurry temperature was maintained at 20° C. for approximately 1 hour. Ethylene oxide was added to the reaction mixture. The reactor was heated to 30° C. Acid was added continuously during a 30 minute heat-up to and 30 minute hold at 60° C. to reach the desired alkali cellulose ratio (AC2). The temperature was then raised to 100° C. and held for 60 minutes to complete the reaction. The reaction mixture was cooled down to ambient temperature and neutralized with sufficient amount of acid to neutralize any excess alkali. The product was then purified, dried, and ground to the desired particle size.

Process C

Cellulose, water, and solvent were charged to a nitrogen-sparged, high pressure reaction kettle per the ratios described in the various tables. The reactor was inerted with nitrogen and pressure tested. The caustic was added and the alkali cellulose slurry temperature was maintained at 20° C. for approximately 1 hour. Acid was added to reach the desired alkali cellulose ratio (AC2). Ethylene oxide was added to the reaction mixture. The reaction mixture was heated to 60° C. over 40 minutes and held at that temperature for 30 minutes. The temperature was then raised to 100° C. for 60 minutes to complete the reaction. The reaction mixture was cooled down to ambient temperature and neutralized with sufficient acid to neutralize any excess alkali. The product was then purified, dried, and ground to the desired particle size.

Process D

Cellulose, water, and solvent were charged to a nitrogen-sparged, high pressure reaction kettle per the ratios described in the various tables. The reactor was inerted with nitrogen and pressure tested. The caustic was added and the alkali cellulose slurry temperature was maintained at 20° C. for approximately 1 hour. Ethylene oxide was added to the reaction mixture. The reactor was heated to 30° C. Acid was added continuously during a 30 minute heat-up to and 30 minute hold at 60° C. in order to reach the desired alkali cellulose ratio (AC2). The temperature was raised to 100° C. and held for 60 minutes. The reactor was then cooled to 50° C. Acid or caustic was added to achieve the desired caustic/cellulose ratio for the hydrophobe reaction (ACHM). The hydrophobe was charged to the reaction mixture. The reactor was heated to 115° C. and maintained for 2.5 hours. The reactor was then cooled to 25° C. to charge the anionic and/or cationic reagents. The reactor was reheated to 60° C. and the temperature was maintained for 2.5 hours. The reaction mixture was cooled down to ambient temperature and neutralized with sufficient acid to neutralize any excess alkali. The product was then purified, dried, and ground to the desired particle size.

Process E

Cellulose, water, and solvent were charged to a nitrogen-sparged, high pressure reaction kettle per the ratios described in the various tables. The reactor was inerted with nitrogen and pressure tested. The caustic was added and the alkali cellulose slurry temperature was maintained at 20° C. for approximately 1 hour. Acid was added to reach the desired alkali cellulose ratio (AC2). The hydrophobe was added to the reactor and mixed. Ethylene oxide was added to the reaction mixture. The reactor was heated to 60° C. over 40 minutes and held at that temperature for 60 minutes. The temperature was then raised to 115° C. and maintained for 90 minutes to complete the reaction. The reactor was then cooled to 40° C. for charging the anionic and/or cationic reagents and any added EO for improving biostability. The reactor was heated to 60° C. and held for 60 minutes. The reaction mixture was cooled down to ambient temperature and neutralized with sufficient acid to neutralize any excess alkali. The product was then purified, dried, and ground to the desired particle size.

Process F

Cellulose, water, and solvents are charged to a nitrogen-sparged, high pressure reaction kettle per the ratios described in the various tables. The reactor is inerted and pressure tested. The caustic is added and the alkali cellulose slurry temperature is maintained at 20 C for approximately 1 hour. Ethylene oxide was added and the temperature was raised to 45° C. and maintained for 45 minutes. The temperature was then raised to 100° C. and held for 60 minutes to complete the reaction. The slurry is cooled down then, a second amount of caustic is added (AC2) and a second alkali cellulose period of 45 minutes at 20° C. is maintained. EO and hydrophobe (if specified) are added then and the temperature is raised to 115° C. and maintained for 2.5 hours. The reaction mixture is cooled down to ambient temperature and neutralized with sufficient acid. The product is then purified, dried, and ground to the desired particle size.

TABLE 1

Sample Preparation Descriptions

| Example | Cellulose Furnish[A] | Cell. Bone Dry (g) | Solvent (g)[B] | Acid Type and Concentration | $H_2O$: $AGU^C$ | NaOH: $AGU^D$ AC1 | NaOH: AGU AC2 | NaOH: AGU ACHM | EO (g) | HM[E] (g) | Cationic or Anionic Agent (g) | Process |
|---|---|---|---|---|---|---|---|---|---|---|---|---|
| 1 Blocky | I | 58 | IPA 667 | 20% acetic in IPA | 16.7 | 1.74 | 1.22 | — | 57.0 | — | — | B |
| 2 Blocky | I | 58 | IPA 667 | 20% acetic in IPA | 16.7 | 1.74 | 1.09 | — | 55.0 | — | — | B |
| 3 Blocky | Ii | 58 | TBA 668 IPA 17.3 Acetone 10.4 | 70% nitric | 12.6 | 1.74 | 1.01 | — | 36.1 | — | — | C |
| 4 Blocky | I | 58 | IPA 667 | 27.5% acetic in IPA | 16.7 | 1.74 | 0.81 | — | 42.3 | — | — | B |

TABLE 1-continued

Sample Preparation Descriptions

| Example | Cellulose Furnish[A] | Cell. Bone Dry (g) | Solvent (g)[B] | Acid Type and Concentration | $H_2O$:AGU[C] | NaOH:AGU[D] AC1 | NaOH:AGU AC2 | NaOH:AGU ACHM | EO (g) | HM[E] (g) | Cationic or Anionic Agent (g) | Process |
|---|---|---|---|---|---|---|---|---|---|---|---|---|
| Comparative 4C | I | 58 | IPA 667 | 35% acetic in IPA | 16.7 | 1.74 | 0.41 | — | 42.2 | — | — | B |
| 5 Blocky | I | 58 | IPA 667 | 20% acetic in IPA | 16.7 | 1.74 | 1.09 | — | 55.4 | — | — | B |
| Comparative 5C | I | 100 | TBA 898 IPA 81 Acetone 29 | 65% nitric | 17.6 | 1.30 | — | — | 71.6 | — | — | A |
| 6 Blocky CMHMHEC (C16) | Ii | 58 | IPA 664 | 20% acetic in IPA (AC2) 50% acetic in IPA (ACHM) | 17.1 | 1.74 | 1.22 | 0.73 | 44.9 | Hexadecyl GE[F] 23.4 | SCA[G] 16 | D |
| 7 Blocky CMHMHEC (C16) | Ii | 58 | IPA 667 | 20% acetic in IPA (AC2) 50% acetic in IPA (ACHM) | 16.7 | 1.74 | 1.09 | 0.49 | 58.1 | Hexadecyl GE 35.1 | SCA 20 | D |
| 8 Blocky HMHEC (C4) | I | 58 | IPA 667 | 20% acetic in IPA (AC2) 50% acetic in IPA (ACHM) | 16.7 | 1.74 | 1.09 | 0.24 | 55.8 | Butyl GE 12.2 | — | D |
| 9 Blocky HMHEC (C12) | iv | 58 | IPA 667 | 20% acetic in IPA | 16.7 | 1.74 | 1.09 | 1.09 | 61.9 | Dodecyl Bromide 23.9 | — | D |
| 10 Blocky HMHEC (C10) | iv | 58 | IPA 667 | 20% acetic in IPA | 16.7 | 1.74 | 1.09 | 1.09 | 61.9 | Decyl Bromide 23.7 | — | D |
| 11 Blocky HMHEC (C4/C16) | iv | 58 | IPA 667 | 20% acetic in IPA (AC2) 50% acetic in IPA (ACHM) | 16.7 | 1.74 | 1.09 | 0.24 | 50.0 | Hexadecyl GE 6.7 Butyl GE 24.4 | — | D |
| 12 Blocky catHMHEC (C16) | iv | 58 | IPA 667 | 20% acetic in IPA (AC2) 50% acetic in IPA (ACHM) | 16.7 | 1.74 | 1.09 | 0.24 | 61.9 | Hexadecyl GE 6.7 | 60% Quat 188[H] 5.94 | D |
| 13 Blocky | ii | 100 | TBA 859 IPA 77 Acetone 28 | 65% nitric | 15.8 | 1.74 | 1.22 | — | 103.3 | — | — | C |
| 14 Blocky | i | 58 | IPA 667 | 12.5% acetic in IPA | 16.7 | 1.74 | 1.34 | — | 83.7 | — | — | B |
| 15 Blocky | ii | 58 | TBA 668 IPA 17.3 Acetone 10.4 | 70% nitric | 12.6 | 1.74 | 1.01 | — | 63.3 | — | — | C |
| 16 Blocky | ii | 58 | TBA 668 IPA 17.3 Acetone 10.4 | 70% nitric | 12.6 | 1.74 | 0.81 | — | 53.0 | — | — | C |
| 17 Blocky | ii | 58 | TBA 668 IPA 17.3 Acetone 10.4 | 70% nitric | 12.6 | 1.74 | 0.61 | — | 53.0 | — | — | C |
| Comparative 17C | ii | 58 | TBA 668 IPA 17.3 Acetone 10.4 | 70% nitric | 12.6 | 1.74 | 0.41 | — | 53.0 | — | — | C |
| 18 Blocky | i | 100 | TBA 898 IPA 81 Acetone 29 | 65% nitric | 15.1 | 0.22 | 1.30 | — | 51.7 / 51.7 | — | — | F |
| 19 Blocky | i | 58 | IPA 667 | 100% acetic | 16.7 | 1.74 | 1.74 | — | 120.4 | — | — | B |
| Comparative 19C | i | 100 | TBA 898 IPA 81 Acetone 29 | 65% nitric | 17.6 | 1.30 | — | — | 136.9 | — | — | A |
| 20 Blocky CMHMHEC (C16) | iii | 58 | TBA 659 IPA 17.2 Acetone 10.3 | 20% acetic in IPA (AC2) 50% acetic in IPA (ACHM) | 13.5 | 1.74 | 1.22 | 0.73 | 56.0 | Hexadecyl GE 49 | SCA 16 | D |
| 21 Blocky CMHMHEC (C16) | ii | 58 | TBA 663 IPA 17.2 Acetone 10.3 | 20% acetic in IPA (AC2) 50% acetic in IPA (ACHM) | 13.5 | 1.74 | 1.22 | 0.73 | 56.1 | Hexadecyl GE 49 | SCA 16 | D |

TABLE 1-continued

Sample Preparation Descriptions

| Example | Cellulose Furnish[A] | Cell. Bone Dry (g) | Solvent (g)[B] | Acid Type and Concentration | $H_2O$: AGU[C] | NaOH: AGU[D] AC1 | NaOH: AGU AC2 | NaOH: AGU ACHM | EO (g) | HM[E] (g) | Cationic or Anionic Agent (g) | Process |
|---|---|---|---|---|---|---|---|---|---|---|---|---|
| 22 Blocky CMHMHEC (C16) | iii | 58 | TBA 678 IPA 17.6 Acetone 10.5 | 85% phosphoric | 10.8 | 1.82 | 1.09 | — | 49.3 12.4 | Cetyl Bromide 6.5 | MCA[I] 20 | E |
| 23 Blocky CMHMHEC C16 | iii | 58 | TBA 645 IPA 16.7 Acetone 10.0 | 85% phosphoric | 16.2 | 1.82 | 1.09 | — | 61.6 12.4 | Cetyl Bromide 8.7 | MCA 20 | E |
| 24 Blocky | i | 500 | TBA 5119 IPA 460 Acetone 167 | 20% nitric | 16.7 | 1.74 | 1.09 | — | 685 | — | — | C |
| Comparative 24C | ii | 100 | TBA 850 IPA 76 Acetone 28 | 65% nitric | 17.6 | 1.30 | — | — | 144.6 | — | — | A |
| 25 Blocky CMHMHEC (C16) | iii | 58 | TBA 662 IPA 16.7 Acetone 10.3 | 85% phosphoric | 13.5 | 1.82 | 1.09 | — | 74.2 12.4 | Cetyl Bromide 8.7 | MCA 20 | E |
| 26 Blocky CMHMHEC | ii | 58 | TBA 662 IPA 16.7 Acetone 10.3 | 85% phosphoric | 21.6 | 1.82 | 1.09 | 0.49 | 74 12.3 | Cetyl Bromide 6.5 | MCA 20 | E |
| 25 Blocky CMHMHEC (C16) | ii | 100 | TBA 850 IPA 76 Acetone 28 | 65% nitric | 15.1 | 0.22 | 1.30 | — | 71.3 100 | Hexadecyl GE 20.7 | — | F |

[A]i Cotton Linter, Intrinsic Viscosity I.V.(dl/g) > 20
ii Wood Pulp, I.V.(dl/g) 4–8
iii Wood Pulp, I.V.(dl/g) 9–12
iv Wood Pulp, I.V.(dl/g) > 18
[B]The solvent weight includes the solvent delivered to the reactor during the acid quench (total solvent).
IPA = Isopropanol
TBA = Tertiary Butyl alcohol
[C]Molar ratio of water to anhydroglucose (AGU)
[D]Molar ratio of sodium hydroxide (NaOH) to anhydroglucose (AGU)
[E]Hydrophobe modification (HM)
[F]GE = Glycidal Ether
[G]SCA = Sodium MonoChloroacetate
[H]Quat 188 = cationizing agent - N-(3-chloro-2-hydroxypropyl)trimethylammonium chloride
[I]MCA = Mono Chloroacetic Acid

EXAMPLES 1-5

The properties for HECs of Examples 1-5 of this invention that have an HE-MS between 1 and 2 are shown in Table 2. Table 1 describes how the non-uniformly substituted HECs are prepared by completely opening up the cellulose fiber with high initial caustic level (AC1) and then "quenching" to an intermediate caustic level (AC2). This process creates regions not accessible to the reactants. Examples 1-5 in Table 2 have an unsubstituted trimer ratio (U3R) greater than 0.21 indicative of a non-uniform structure. Furthermore, the fiber rating for these blocky HECs is low (less than 6) indicating that the reaction is homogeneous on a macroscopic level instead of heterogeneous as for example, a mixture of highly substituted HEC and unsubstituted cellulose fibers would appear. The fiber rating is determined by comparing the 1 wt % HEC solutions to cellulose fiber solution standards that have been prepared with cut cotton linters. The ratings 1, 2, 3, 4, 5, and 6 correspond to 0.4, 1.4, 3.2, 6.9, 11.4, 16 ppm fiber concentration, respectively.

HECs that have good solution properties and unsubstituted trimer ratios greater than 0.21 are the basis of this invention. Comparative Examples 4C and 5C as well as several commercial samples with HE-MS between 1 and 2 have a U3R well below 0.21 indicating a more uniform substitution along the polymer backbone.

In addition, it has been found that the second caustic to AGU molar ratio (AC2) should be greater than about 0.6 to induce a blocky structure with good solution properties. Example 4 and Comparative Example 4C show a dramatic change in the structure as the second caustic to AGU molar ratio is reduced from 0.8 to 0.4. The unsubstituted trimer ratio drops significantly from 0.30 to 0.16. Furthermore, the viscosity of the solution drops from 21,800 cPs to 10,100 cP indicating a less associative structure consistent with a more uniform distribution as measured by the low unsubstituted trimer ratio.

Examples 1, 2, 4, and 5 show that high molecular weight blocky HECs produced from cotton linters have 1 wt %. Brookfield viscosities (spindle 3, 3 rpm, at 25° C.) up to 25,000 cps. Commercially available high molecular weight HECs such as those marketed under the trademarks Natrosol 250 HHBR & HHR, Cellosize QP 100 MH, and Tylose H 200000 YP2 products typically have 1 wt % viscosities in the range of 4,500-6,000 cP. Furthermore, the HEC solutions of the present invention have elasticities (G's) an order of magnitude greater than commercially available high molecular weight HEC (see Table 2 and 3).

Example 3 is a blocky HEC produced from a low molecular weight wood pulp starting material. The synthesis procedure was performed on a wide range of furnishes from cotton linters to wood pulps in order to generate a family of blocky HEC products.

TABLE 2

HEC with HE-MS 1-2

| Example | HE-MS | 1% Aq. Viscosity (cP) | G' at 0.1 Hz | Fiber Count | Unsubstituted Trimer Ratio U3R |
|---|---|---|---|---|---|
| 1 Blocky HEC | 1.4 | 18,600 | 5.6 | 3 | 0.279 |
| 2 Blocky HEC | 1.3 | 25,000 | 8.1 | 2 | 0.382 |
| 3 Blocky HEC | 1.8 | 191 @ 2 wt % | | 1 | 0.464 |
| 4 Blocky HEC | 1.3 | 21,800 | | 3 | 0.301 |
| Comparative 4C | 1.3 | 10,100 | | 1 | 0.157 |
| 5 Blocky HEC | 1.7 | 14,400 | | 1 | 0.218 |
| Comparative 5C | 1.6 | 1,860 | | 1 | 0.131 |
| Comparative Natrosol 150GXR | 1.5 | 200 @ 2 wt % | | 1 | 0.191 |
| Comparative Natrosol 150GBXR | 1.6 | 185 @ 2 wt % | | 1 | 0.031 |
| Comparative Natrosol 180GXR | 1.8 | 325 @ 2 wt % | | 1 | 0.167 |
| Comparative Cellosize QP30000H | 1.9 | 1,800 | | 1 | 0.196 |
| Comparative Cellosize EP 09 | 2.0 | 100 @ 5 wt % | | 1 | 0.167 |

EXAMPLES 6-12

Blocky HECs provide a unique template for further derivatization with hydrophobe, cationizing reagents, anionizing reagents, cross-linkers, and polyethylene oxide chain extenders. As shown in Table 2a, Examples 6-12 are various derivatives of blocky HECs with HE-MS between 1 and 2. Examples 6 and 7 contain cetyl hydrophobe and carboxymethyl modification. Example 8 and 10 describe hydrophobe-modified blocky HECs with U3Rs of 0.45 and 0.255, respectively. Examples of blocky HECs with $C_{12}$, $C_{10}$, and mixed $C_4/C_{16}$ hydrophobes, and with a cationic charge are shown in Table 2a as examples 9-12. All of these derivatized blocky HEC samples have a low fiber rating.

TABLE 2a

Derivatized HEC with HE-MS 1-2

| Example | HE-MS | HM (%) | Charge (DS) | 1% Aq. Viscosity (cP) | Fiber Count | Unsubstituted Trimer Ratio U3R |
|---|---|---|---|---|---|---|
| 6 Blocky CMHMHEC (C16) | 1.3 | 0.21 | 0.25 | 13 | 1 | N/A |
| 7 Blocky CMHMHEC (C16) | 1.7 | 1.2 | 0.17 | 210 | 1 | N/A |
| 8 Blocky HMHEC (C4) | 1.5 | 2.6 | — | 13,460 | 3 | 0.450 |
| 9 Blocky HMHEC (C12) | 1.8 | 1.4 | — | 28,400 | 2 | Not measured |
| 10 Blocky HMHEC (C10) | 1.7 | 1.8 | — | 15,800 | 2 | 0.255 |
| 11 Blocky HMHEC (C4/C16) | 1.4 | 0.8/0.3 | — | 29,540 | 1 | Not measured |
| 12 Blocky cat HMHEC (C16) | 1.7 | 0.5 | 0.01 | 40,0000 | 1 | 0.380 |

EXAMPLES 13-19

The most common commercial HECs have an HE-MS in the range of 2 to 3. Table 3 shows that blocky HECs can be produced in this HE-MS range. For comparison, all commercial and Comparative Examples have a U3R less than 0.21 indicating a more uniform structure.

Example 14 shows that high molecular weight blocky HEC with an HE-MS of 2.3 exhibits a significantly higher viscosity than commercially available HEC in the same HE-MS range.

As is the case for HECs in the HE-MS range of 1-2, the second caustic to AGU molar ratio (AC2) should be greater than about 0.6 to induce blocky HECs that form good solutions with low fiber rating in the HE-MS range of 2-3. Example 17 and Comparative Example 17C demonstrate a dramatic change in the structure as the second caustic level is reduced from 0.6 to 0.4 mole NaOH/mole AGU. The unsubstituted trimer ratio drops significantly from 0.31 to 0.10. Furthermore, the fiber content of Comparative Example 17C increases.

Another process that produces the blocky structure is demonstrated in Example 18. In this case, an ethylene oxide reaction at extremely low caustic level (AC1 0.22 mole NaOH/mole AGU) was used to partially open up the cellulose fiber before reacting additional ethylene oxide at an AC2 of 1.3 mole NaOH/mole AGU. The U3R of this Example is 0.40 indicating that it is a HEC with a blocky structure.

In Example 19, the reaction takes place at a single, very high caustic to AGU molar ratio. Although this process is disclosed in this Example, it is not preferred because of the poor reaction efficiencies. Notwithstanding, it still produced an extremely blocky HEC with a U3R of 0.71.

TABLE 3

HEC with HE-MS 2-3

| Example | HE-MS | 1% Aq. Viscosity (cP) | G' at 0.1 Hz | Fiber Count | Unsubstituted Trimer Ratio U3R |
|---|---|---|---|---|---|
| 13 Blocky HEC | 2.3 | 18 | | 4 | 0.324 |
| 14 Blocky HEC | 2.3 | 18,860 | 5.3 | 3 | 0.233 |
| 15 Blocky HEC | 3.0 | 14 | | 1 | 0.456 |
| 16 Blocky HEC | 2.6 | 11 | | 1 | 0.364 |
| 17 Blocky HEC | 2.6 | 10 | | 3 | 0.313 |
| Comparative 17C | 2.6 | 14 | | >6 | 0.100 |
| 18 Blocky HEC | 2.5 | 600 | | 5 | 0.401 |
| 19 Blocky HEC | 2.9 | 2,640 | | 1 | 0.710 |
| Comparative 19C | 3.0 | 2,980 | | 4 | 0.114 |
| Comparative Tylose H200 X | 2.2 | 200 @ 1.9 wt % | | 1 | 0.134 |
| Comparative Natrosol 210 HI-VIS | 2.5 | 5,200 | | 1 | 0.124 |

TABLE 3-continued

HEC with HE-MS 2-3

| Example | HE-MS | 1% Aq. Viscosity (cP) | G' at 0.1 Hz | Fiber Count | Unsubstituted Trimer Ratio U3R |
|---|---|---|---|---|---|
| Comparative Cellosize QP10000H | 2.7 | 4,800 | 0.65 | 1 | 0.147 |
| Comparative Natrosol 250 HHR-P | 2.3 | 6,100 | 0.20 | 1 | 0.155 |
| Comparative Natrosol 250 HHR | 2.6 | 4,200 | 0.20 | 1 | 0.113 |
| Comparative Cellosize HEC-25 | 2.8 | 4,500–6,000 | | 1 | 0.072 |
| Comparative Natrosol 250 H | 2.5 | 2,300 | | 1 | 0.158 |
| Comparative Tylose H100000 YP | 2.6 | 100,000 @ 1.9 wt % | | 1 | 0.152 |

EXAMPLES 20-23

Table 3a details blocky HECs with an HE-MS in the range of 2 to 3 that have been further modified with hydrophobic and/or anionic reagents. Examples 20 and 21 have extremely high Brookfield viscosities and elasticities (G') consistent with strong associative network formation.

TABLE 3a

Derivatized HEC with HE-MS 2–3

| Example | HE-MS | HM (%) | Charge (DS) | 1% Aq. Viscosity (cP) | G' at 0.1 Hz | Fiber Count | Unsubstituted Trimer Ratio U3R |
|---|---|---|---|---|---|---|---|
| 20 Blocky CMHMHEC (C16) | 2.1 | 2.2 | 0.20 | 65,100 | 10 | 1 | N/A |
| 21 Blocky CMHMHEC (C16) | 2.2 | 2.6 | 0.22 | 84,600 | 32 | 1 | N/A |
| 22 Blocky CMHMHEC (C16) | 2.3 | 0.7 | 0.34 | 100 | | 1 | N/A |
| 23 Blocky CMHMHEC (C16) | 2.8 | 1.0 | 0.30 | 15120 | | 1 | N/A |

EXAMPLE 24

Example 24 in Table 4 demonstrates that a blocky HEC can be produced having an HE-MS above 3. This sample has an HE-MS of 3.8 yet still exhibits an U3R of 0.35 and has good solution properties with low fiber rating. In comparison, Comparative Example 24C, an HEC made by a regular process (caustic to AGU molar ratio AC1=1.30), has an U3R of 0.19 which is characteristic of a more uniform structure. Also shown in this Table are several commercial HECs with high HE-MS that have extremely low unsubstituted trimer ratios. These low U3Rs are consistent with a high degree of biostability as stated in the literature for Cellosize ER (enzyme resistant), Natrosol B (biostable), and Tylose HS type HECs products.

TABLE 4

HEC with HE-MS > 3

| Example | HE-MS | 1% Aq. Viscosity (cP) | Fiber Count | Unsubstituted Trimer Ratio U3R |
|---|---|---|---|---|
| 24 Blocky HEC | 3.8 | 8 | 2 | 0.351 |
| Comparative 24C | 3.6 | 330 @ 2 wt % | 3 | 0.191 |
| Comparative Tylose HS 30000 YP2 | 3.1 | Not measured | | 0.025 |
| Comparative Natrosol 250 HBR | 3.2 | 2,200 | 1 | 0.057 |
| Comparative Natrosol 250 HHBR | 3.3 | 5,300 | 1 | 0.036 |
| Comparative Cellosize ER30000 | 3.7 | Not measured | | 0.026 |
| Comparative Cellosize ER52000 | 3.9 | Not measured | | 0.028 |
| Comparative Cellosize ER15000 | 3.9 | Not measured | | 0.026 |

EXAMPLES 25-27

Table 4a shows examples of derivatized blocky HECs that have an HE-MS greater than 3. Examples 22, 25 and 26 demonstrate that a range of water ratios in the process (shown in Table 1) can be used to produce the blocky structure. Example 27 shows that the reverse process can be used to produce a hydrophobe-modified blocky HEC as indicated by a U3R of 0.27.

TABLE 4a

Derivatized HEC with HE-MS > 3

| Example | HE-MS | HM (%) | Charge (DS) | 1% Aq. Viscosity (cP) | Fiber Count | Unsubstituted Trimer Ratio U3R |
|---|---|---|---|---|---|---|
| 25 Blocky CMHMHEC (C16) | 3.4 | 0.8 | 0.3 | 12,760 | 1 | N/A |

TABLE 4a-continued

| | Derivatized HEC with HE-MS > 3 | | | | | |
|---|---|---|---|---|---|---|
| Example | HE-MS | HM (%) | Charge (DS) | 1% Aq. Viscosity (cP) | Fiber Count | Unsubstituted Trimer Ratio U3R |
| 26 Blocky CMHMHEC (C16) | 3.4 | 0.8 | 0.2 | 99 | 1 | N/A |
| 27 Blocky HMHEC (C16) | 4.3 | 1.8 | | 3,360 | Hazy | 0.274 |
| Comparative Natrosol Plus 330 5 lots | 3.8 | 0.8 | | 300 | 1 | 0.010 ± 0.0060 |

EXAMPLE 28

Architectural Coatings

Blocky HECs show enhanced thickening efficiency in architectural coating applications. Blocky HEC Example 2 and Natrosol 250 HHR product were evaluated in the following Ucar Latex 367 60-PVC flat paint formulation. The blocky HEC thickener was 19% more efficient than the Natrosol 250 HHR product and provided a slight increase in high shear viscosity (HSV). Data is shown in Table 6.

| Ucar Latex 367 60 PVC Formulation | |
|---|---|
| | Grams |
| Pigment Grind | |
| Water | 1,696 |
| Tamol 731 Dispersant | 62 |
| KTPP | 13.6 |
| Igepal CO-660 | 29.9 |
| AMP-95 | 13.6 |
| Propylene Glycol | 234.8 |
| Rhodoline 640 | 25.8 |
| Water, Discretionary (Added as needed) | 1,260 |
| TiPure R-931 Titanium Dioxide | 2,035 |
| Satintone W Calcined Clay | 1,696 |
| # 10 White Calcium Carbonate | 2,714 |
| Dispersed to Hegman 4 to 5-Letdown | |
| Ucar Latex 367 | 3,071 |
| Texanol Coalescent | 107.2 |
| Rhodoline 640 | 25.8 |
| Proxel GXL Preservative | 13.6 |
| | 13,000 |
| Thickened Paints: | |
| Base Paint | 230 g |
| Thickener + Water to 100 KU | 50 g |
| Total: | 280 g |
| Stormer, Initial | 95 KU |
| pH, Initial | 8 |
| Solids, Weight % | 52 |
| Volume % | 32 |
| PVC | 60.2 |
| Lb/Gal | 11.66 |

TABLE 6

| UCAR Latex 367 60 PVC Flat Paint Properties | | | | | | |
|---|---|---|---|---|---|---|
| Thickener | Thickener Conc. (wt %) | Stormer (KU) Initial/ Overnight | HSV (Poise) | Sag | Leveling | Hiding |
| Natrosol 250HHR | 0.43 | 95/97 | 0.6 | 10 | 5 | 0.987 |
| Invention Example 2 | 0.36 | 96/100 | 0.7 | 14 | 4 | 0.988 |

Hydrophobically-modified hydroxyethyl cellulose (HM-HEC) is an important product used in the paint industry. There are many characteristics that this rheology modify provides to a paint formulation, such as spatter free paint application, solution stability, and thickening efficiency. It is generally used in conjunction with another thickener that provides improved brush viscosity (high shear viscosity, HSV). It would simplify the formulation to be able to use a HMHEC as the sole thickener to provide all of the important attributes. Hydrophobically modified blocky HECs are an improvement over a typical HMHEC, such as Natrosol Plus 330 product, by providing an improved high shear viscosity as well as other critical attributes.

The rheology modifiers of the present invention were tested as follows either in the Ucar Latex 379G 70-PVC or Ucar Latex 367 60-PVC formulations. The data in Table 7 indicates that the blocky HMHECs provide high shear viscosities 44-67% higher with comparable or better paint properties as compared to Natrosol Plus 330 product.

| Ucar Latex 379G 70-PVC Formulation | |
|---|---|
| Base Paint | Grams/13,000 g |
| Pigment Grind | |
| Water | 2,521 g |
| Nuosept 95 | 32.4 |
| Tamol 731A Dispersant | 64.7 |
| Igepal CO-660 | 31.0 |
| Igepal CO-897 | 43.6 |
| AMP-95 | 14.1 |
| Propylene Glycol | 182.9 |
| Rhodine 640 | 14.1 |
| Water, Discretionary, | 1,407 |
| Ti-Pure R-931 TiO2 | 1,055 |

-continued

Ucar Latex 379G 70-PVC Formulation

| Base Paint | Grams/13,000 g |
|---|---|
| ASP NC Clay | 2,814 |
| ECC #10 White Calcium Carbonate | 2,110 |
| Celite 281 Silica | 352 |
| -Disperse to Hegman 4 to 5- | |
| Letdown | |
| -All Discretionary Water in- | |
| Ucar Latex 379G | 2,079 |
| Texanol | 11.1 |
| PA-454 Antifoam | 26.7 |
| Propylene Glycol | 140.7 |
| Total | 13,000 g |

| Thickened Paints | |
|---|---|
| Base Paint | 220 g |
| Thickener Solution + Water to 95 KU | 50 |
| Total | 270 g |
| pH, initial (8.5 Target) | |
| Density, lb/100 gal | 11.3 |
| Solids, Weight % | 47.8 |
| Volume % | 29.3 |
| PVC, % | 69.9 |

TABLE 7

Paint Properties for Hydrophobically Modified Blocky HEC

| Thickener | Paint Formulation | Thickener Conc. (wt %) | HSV (Poise) | Spatter | Leveling | Sag | Hiding |
|---|---|---|---|---|---|---|---|
| Natrosol Plus 330 | UCAR 379G 70 PVC | 0.66 | 0.9 | 9 | 2 | 18 | 0.98 |
| Invention Example 7 | UCAR 379G 70 PVC | 0.67 | 1.3 | 9 | 3 | 14 | 0.98 |
| Natrosol Plus 330 | UCAR 367 60 PVC | 0.54 | 0.9 | 9 | 2 | 23 | 0.98 |
| Invention Example 26 | UCAR 367 60 PVC | 0.57 | 1.5 | 8 | 2 | 23 | 0.98 |

EXAMPLE 29

Construction

Blocky HECs show enhanced viscosity in joint compounds. Blocky HEC Example 2 and Natrosol 250HHR product were evaluated as thickeners at 0.30 wt % in an all-purpose joint compound formulation, as described below. Table 8 shows that the formulation containing blocky HEC was 23% more efficient (joint compound viscosity) while maintaining good adhesion, workability, and cratering properties.

All-Purpose Joint Compound Formulation

| Ingredients | Supplier | Wt % |
|---|---|---|
| Ground CaCO3 | Georgia White #9 | 61 |
| Attapulgite Clay | Gel B, Milwhite | 2.0 |
| Mica | 4-K, Oglebay Norton | 3.00 |

-continued

All-Purpose Joint Compound Formulation

| Ingredients | Supplier | Wt % |
|---|---|---|
| Latex dispersion | EVA or PVA latex (see Note 1) | 2.5 |
| Propylene glycol | Aldrich | 0.35 |
| Biocide | Trosan 174, Troy chemical | 0.05 |
| Defoamer | Foamaster PD1WD, Cognis | 0.02 |
| Thickener | | 0.30 |
| Water | Tap water | 30.6 |
| Total | | 100 |

TABLE 8

All Purpose Joint Compound Properties

| Thickener | Joint Compound Viscosity (Brabender Units) | Adhesion | Cratering (1–10) 10 best | 5 months aging |
|---|---|---|---|---|
| 250HHXR Commercial HEC | 480 | 100% | 7 | failed |
| Invention Example 2 | 590 | 100% | 8 | excellent |

Butyl-modified blocky HEC shows superior adhesion in lightweight joint compounds. Derivatized blocky HEC Example 8 and Nexton J20R product were evaluated as thickeners at 0.4 wt % in a lightweight joint compound formulation as shown below. Nexton J20R is a commercial modified HEC and was chosen as a control as it is commonly used in lightweight joint compound applications. Table 9 shows the joint compound with Example 8 had better adhesion and similar properties in thickening efficiency (high BU), cracking, and water retention as compared to the commercial Nexton J20R product.

Light Weight Joint Compound Formulation

| Material | Wt % |
|---|---|
| Georgia White #9 CaCO3 | 49.25 |
| Attapulgite Clay (Gel B) | 3.2 |
| SilCell 35/34 Treated Perlite | 4.75 |
| Cellulosic Thickener | 0.40 |
| Latex or Dispersible powder | 1.3 (active) |
| Biocide (Troysan 174) | 0.1 |
| Water | 41.0 |
| Total | 100 |

TABLE 9

Lightweight Joint Compound Properties

| Polymer Sample | Joint Compound Viscosity (BU) | Workability* | Water Retention (%) | Cratering at RT* | Cracks* 110F/20% RH | Adhesion (%) USG/NG Tape |
|---|---|---|---|---|---|---|
| Nexton J20R Control | 435 | 4.5 | 92.7 | 4 | 3.5 | 62/56 |
| Invention Example 8 | 465 | 3.5 | 92.2 | 3 | 4 | 95/93 |

*Scale 1–5, 5 best

Blocky HEC and derivatized blocky HEC can be used to replace clay in joint compounds. Blocky HEC and derivatized blocky HEC were evaluated in a clay-free joint compound formulation. Clay is a natural product with inconsistent performance and it generates cracks and craters in joint compounds. However, without the clay, joint compounds have poor sag resistance and less body. Examples 2 and 20 were tested at 0.5 wt % as the sole rheology modifier in the clay-free joint compound system with reduced mica levels as shown. These were compared with Natrosol 250 HHXR product. Table 10 shows the joint compound containing the Natrosol 250 HHXR product had poor sag resistance, open time, and workability, confirming the need for a structure builder like clay. On the other hand, Examples 2 and 20 produced excellent joint compounds with properties that are typically obtained with thickener and a full complement of attapulgite clay.

Typical All-Purpose Joint Compound Formulation with and without Clay

| Ingredient | Use Level(s) discussed herein | "Typical" Use Levels |
|---|---|---|
|  | Regular weight | Regular weight |
| Water | 30–31% | 30–31% |
| Ground CaCO3 | 64% | 62–64% |
| Attapulgite clay |  | 1.7–2.5% |
| Mica | 1.5% | 5–8% |
| Biocide | 0.1% | 0.1% |
| Latex, PVA | 2.5% | 2.5% |
| Thickener | 0.5% | 0.4–0.5% |

EXAMPLE 30

Paper

Blocky HEC is a highly efficient water retention agent in paper coatings. Blocky HEC Example 3, commercial samples Aqualon 7L1T CMC, and Natrosol 250GR were evaluated as thickeners and water retention aids in the paper coating formulation as shown below. The amount of rheology modifier necessary to maintain the Brookfield viscosity at 1500±50 cps, the water loss, and Hercules high shear viscosity are shown in Table 11. Blocky HEC Example 3 and HEC 250GR are of similar molecular weights and solution viscosities; however, the blocky product has a significantly higher dosage efficiency than HEC 250GR while maintaining its low water loss rate. In addition, blocky HEC Example 3 has much lower water loss and higher dosage efficiency than Aqualon 7L1T CMC yet similar desirable high shear rheology.

Paper coating formulation

|  | Parts |
|---|---|
| HC 60* | 60 |
| HC 90* | 40 |
| Dow 620 SB latex | 12 |
| Calcium stearate | 1.00 |
| Dispex N-40 (dispersing agent) | 0.25 |
| Solids (%) | 68 +/− 0.5 |
| Viscosity (cps): | 1500 cps at ambient |
| Rheology modifier | Aqualon CMC7L1T, HEC 250GR, Invention Example 3 |

*Ground Calcium Carbonate (HydroCarb) from OMYA Inc.

TABLE 10

All-Purpose Clay-free Joint Compound Properties

| WSP | JC Viscosity (BU) | Adhesion | Pocking | Cracking | *Workability | *Open Time | Apperance | Sag Resistance |
|---|---|---|---|---|---|---|---|---|
| Invention Example 20 | 270 | 94% | 9 | 9 | 9 | 8 | 8 | 9 |
| Invention Example 2 | 450 | 94% | 6 | 9 | 9+ | 8 | 9 | 9+ |
| Natrosol 250HHXR | 280 | 17% | 7 | 8 | 4 | 4 | 9 | 2 |

*The scale for these properties is from 1 to 10 with 10 being the best.

TABLE 11

Paper Coating Properties

| Thickener | HE-MS or DS | 2% Viscosity (cPs) | Parts thickener/ 100 part filler | Water Loss (g/sq meter, 0.6 Bar/1 min | High Shear Rheology 1$^{st}$ Pass 2400/4400 RPM | High Shear Rheology 2$^{nd}$ Pass 2400/4400 RPM |
|---|---|---|---|---|---|---|
| Natrosol HEC 250 G | 2.5 | 300 | 0.75 | 91 | 84/56 | 54/48 |
| Aqualon 7L1T CMC | 0.7 | 100 | 0.99 | 168 | 42/34 | 34/30 |
| Invention Example 3 | 1.8 | 191 | 0.52 | 98 | 49/37 | 41/35 |

EXAMPLE 31

Personal Care

Blocky HEC shows enhanced viscosity in personal care formulations. Natrosol® hydroxyethyl cellulose type 250HHR and blocky HEC Example 2 were compared at 0.7 wt % for thickening efficiency in the hair conditioner formulation shown below.

| Hair Conditioner | |
|---|---|
| 90.94 g | Deionized water |
| 00.70 g | Thickening polymer (Natrosol ® 250HHR, blocky HEC example 2) |
| 02.00 g | Cetyl alcohol |
| 00.50 g | Potassium Chloride |
| 02.00 g | Isopropyl Myristate |
| As required | citric acid to adjust pH |
| As required | Sodium hydroxide to adjust pH |
| 00.50 g | Germaben II |

Procedure:

The thickening polymer was added to water under agitation. Next, the pH was adjusted to 8.0 to 8.5. The slurry was stirred for at least 30 minutes or until the polymer dissolved. The solution was heated to about 65° C. and cetyl alcohol was added and mixed until homogeneous. The mixture was cooled to about 50° C. and potassium chloride was added. Isopropyl myristate was added and mixed until the mixture looked homogeneous. The pH of the mixture was adjusted to 5.3-5.5 with citric acid and/or NaOH solution. The conditioner was preserved with 0.5 g Germaben II and mixed until the mixture reached room temperature.

The viscosity of the conditioning formulation containing blocky HEC Example 2 was 1,550 cP, as compared to the control containing Natrosole 250HHR at 910 cPs, a 70% improvement in thickening efficiency.

Hydrophobically modified blocky HECs show enhanced viscosity stability in oil-in-water emulsions. They were evaluated as a polymeric emulsifier/stabilizer in a typical emulsion formulation shown. Examples 20 and 21 were compared against commercial polymeric emulsifiers (Natrosol Plus 330, 331, and PolySurf 67). In addition, Pemulen TR-1, Pemulen TR-2 and Carbopol ETD 2020 products, commonly used hydrophobically modified acrylate cross-polymers, were included in the comparison. Table 12 and 13 show the viscosity data for one-month storage at room temperature and 40° C., respectively. Examples 20 and 21 have dramatically improved emulsifying and stabilizing properties over the commercial hydrophobically modified HECs. Furthermore, the emulsifying/stabilizing efficiency is near that of Pemulen TR-1, Pemulen TR-2, and Carbopol ETD 2020, which are extremely efficient emulsifying/stabilizing polymers in the market. The thickening efficiency is even better than that of Pemulen TR-2.

| Composition of Basic Emulsion Formulation | |
|---|---|
| Ingredients | Wt % |
| Distilled water | q.s. to 100.0 |
| Polymeric emulsifier/stabilizer | 0.5–1.00 |
| Carnation oil (mineral oil) | 10.00 |
| Germaben II (preservative) | 0.20 |

Procedure:
Prepare stock solution of polymeric emulsifier/stabilizer
Add mineral oil to the aqueous phase and Germaben II
Mix the formulation with Braun kitchen mixer for 3 minutes at speed 5.
(All emulsions prepared had a pH 5–7)

TABLE 12

Viscosity stability of oil-in-water emulsions upon 4 weeks storage at room temperature

| | | Viscosity (mPa · s; spl/rpm C/10) | | | | | |
|---|---|---|---|---|---|---|---|
| Polymer | Wt % | 24 hrs | 3 days | 1 wk | 2 wks | 3 wks | 4 wks |
| Blank (without polymer) | — | 10 (2/30) | Phase sep | Phase sep | Phase sep | Phase sep | Phase |
| Carbopol ETD 2020 | 0.5 | 23200 | 25100 | 25900 | 26800 | 25100 | 24700 |
| | 1.0 | 58400 | 63000 | 59500 | 62000 | 62200 | 63000 |
| Pemulen TR-1 | 0.5 | 13400 | 13400 | 13000 | 13400 | 11700 | 11600 |
| Pemulen TR-2 | 0.5 | 2280* | 2180* | 2140* | 2080* | 2120* | 2100* |
| Natrosol Plus 330 | 1.0 | 1200* | 880* | 920* | Phase sep | Phase sep | Phase sep |
| Natrosol Plus 331 | 1.0 | 2880* | 1660* | 780* | 600* | Phase sep | Phase sep |
| Polysurf 67 | 1.0 | 17400 | 15100 | 14100 | 13700 | 13600 | 13400 |
| Invention Example 20 | 0.5 | 9000 | 8000 | 7000 | 8200 | 8100 | 8000 |
| | 1.0 | 28300 | 27000 | 22500 | 26600 | 25000 | 24600 |

TABLE 12-continued

Viscosity stability of oil-in-water emulsions upon 4 weeks storage at room temperature

| Polymer | Wt % | Viscosity (mPa · s; spl/rpm C/10) | | | | | |
|---|---|---|---|---|---|---|---|
| | | 24 hrs | 3 days | 1 wk | 2 wks | 3 wks | 4 wks |
| Invention Example 21 | 0.5 | 5700 | 5500 | 6000 | 7000 | 7000 | 7000 |
| | 1.0 | 21300 | 21500 | 23500 | 25900 | 25800 | 25600 |

*spl/rpm 3/30

TABLE 13

Viscosity stability of oil-in-water emulsions upon 4 weeks storage at 40° C.

| Polymer | Wt % | Viscosity (mPa · s; spl/rpm C/10) | | | | | |
|---|---|---|---|---|---|---|---|
| | | 24 hrs | 3 days | 1 wk | 2 wks | 3 wks | 4 wks |
| Blank (without polymer) | — | 10 (2/30) | Phase sep | Phase sep | Phase sep | Phase sep | Phase |
| Carbopol ETD 2020 | 0.5 | 23200 | 28000 | 28600 | 26700 | 26600 | 25500 |
| | 1.0 | 58400 | 69500 | 61100 | 60800 | 61200 | 61300 |
| Pemulen TR-1 | 0.5 | 13400 | 13000 | 13400 | 13400 | 12100 | 12050 |
| Pemulen TR-2 | 0.5 | 2280* | 2320* | 2200* | 2200* | 2020* | 2000* |
| Natrosol Plus 330 | 1.0 | 1200* | 920* | Phase sep | Phase sep | Phase sep | Phase sep |
| Natrosol Plus 331 | 1.0 | 2880* | 1080* | 1000* | Phase sep | Phase sep | Phase sep |
| Polysurf 67 | 1.0 | 17400 | 14300 | 13400 | 12800 | 12600 | 12200 |
| Example 20 | 0.5 | 9000 | 8000 | 8000 | 8500 | 8300 | 8300 |
| | 1.0 | 28300 | 25000 | 22500 | 25300 | 24900 | 24200 |
| Example 21 | 0.5 | 5700 | 6000 | 7000 | 7700 | 7800 | 7700 |
| | 1.0 | 21300 | 25000 | 26000 | 27200 | 27600 | 27600 |

*spl/rpm 3/30

Examples 20 and 21 were evaluated in the surfactant formulation shown to investigate compatibility in general personal care and household applications. Example 20 and 21 were compared against commercial rheology modifiers Natrosol Plus 330, and PolySurf 67 products. In addition, Carbopol ETD 2020 product was included in the comparison. Table 14 shows that the hydrophobically modified blocky HEC Examples 20 and 21 are very efficient cellulosic thickeners. Example 21 resulted in clear solutions unlike any of the others tested.

Composition of basic surfactant formulation

| Ingredients | Wt % | Ingredients | Wt % |
|---|---|---|---|
| Texapon 28 | 25.00 | Sodiumlaurylether sulfate (SLES) | 7.00 |
| Plantacare 2000 UP | 5.00 | Decyl Glucoside (APG) | 2.65 |
| Tegobetaine L7 | 10.00 | Cocamidopropylbetaine (CAPB) | 3.10 |
| Thickener | —.— | Thickener | —.— |
| Citric acid | pH 5.5–6.5 | Citric acid | pH 5.5–6.5 |
| Germaben II | 0.20 | Germaben II | 0.20 |
| Water | q.s. to 100.00 | Water | q.s. to 100.0 |

Procedure:
Dissolve thickener in demineralized water.
Add Texapon 28 to thickener solution and mix homogeneously.
Add Plantacare 2000 UP to thickener solution and mix homogeneously.
Add Tegobetaine L7 to thickener solution and mix homogeneously.
Adjust pH with citric acid to 5.5–6.5.
Add Germaben II.

TABLE 14

Viscosity and appearance of surfactant formulation with thickener

| Polymer | | Brookfield viscosity (mPa · s, spd/rpm 3/30) | Appearance |
|---|---|---|---|
| Polysurf 67 CS | 0.75 wt % | 1260 | Very hazy |
| | 1.00 wt % | 3400 | Very hazy |
| | 1.25 wt % | 6200* | Very hazy |
| Natrosol Plus 330 CS | 1.00 wt % | 1040 | Slightly hazy |
| | 1.15 wt % | 1500 | Slightly hazy |
| | 1.30 wt % | 2500 | Slightly hazy |
| | 1.50 wt % | 3400 | Hazy |
| Carbopol ETD 2020 | 0.50 wt % | 1240 | Hazy |
| | 0.60 wt % | 2300 | Very hazy |
| | 0.65 wt % | 3160 | Very hazy |
| Invention Example 20 | 0.75 wt % | 2160 | Very hazy |
| | 0.90 wt % | 5000* | Very hazy |
| Invention Example 21 | 0.75 wt % | 1360 | Clear |
| | 1.00 wt % | 5500* | Clear |

*spl/rpm is 4/30

Examples 20 and 21 were evaluated as a gelling agent in an aqueous solution for hair styling gels. In addition, Carbopol Ultrez 10 (carbomer) and Carbopol ETD 2020 (C10-C30 modified acrylate), Natrosol 250 HHR, Natrosol 250 HR and Klucel H, commonly used gelling agents were included in the comparison.

The thickening efficiency and suspending power of Examples 20 and 21 was better than that of commercial HECs and HPC. Furthermore, example 21 showed a carbopol like texture (stiff and elastic gel), while the others were considered as flowable gels. The electrolyte tolerance of examples 20 and 21 was better compared to Carbopol Ultrez 10 and Carbopol ETD 2020.

EXAMPLE 32

Completion/Workover Fluids

The HEC of the invention exhibits novel thickening of heavy brines. Completion fluids are composed of a variety of brines of different salinity characterized by a density ranging from 8.5 ppg (pound per gallon) for seawater up to 19.2 ppg for heavy brines containing zinc and calcium bromide salts. Standard high viscosity HEC is commonly used as a viscosifier for brines ranging from 9-13 ppg. There presently is not an efficient viscosifier for heavy brines with a density ranging from 14 ppg ($CaBr_2$) to 19.2 ppg ($ZnBr_2/CaBr_2$). These brines have a very low level of free water content available, and therefore, do not promote optimum hydration of standard HECs. These brines are characterized by a very low pH (pH<1 for $ZnBr_2/CaBr_2$).

Blocky HEC Example 2 was evaluated in 4 different brine systems (freshwater, salt-saturated water, $CaBr_2$ and $ZnBr_2/CaBr_2$) at 0.57 wt %. These were compared to a standard HEC widely used in completion fluids (Natrosol HI-VIS). The viscosity and fluid loss properties were measured after static aging overnight at room temperature (Tables 15a-d).

Blocky HEC Example 2 showed exceptional thickening in the high density, heavy brine solutions (characterized by low water activity) as detailed by the high apparent viscosities (A.V.) and yield values (Yv) that developed in these systems (Tables 15c-d). In contrast, commercial HI-VIS did not go into solution in these low water activity systems. Additionally, the blocky HEC sample developed appreciable low-end rheology as reflected by the 6 and 3-rpm Fann dial readings (DR), and showed appropriate fluid loss (F.L.) values.

TABLE 15-a

Rheology/FL performance of various HEC samples in Demineralized water

| Fluid System | | | | Final | Fann DR | | Rheology | | | Fluid Loss |
|---|---|---|---|---|---|---|---|---|---|---|
| Brine | Density ppg | Initial pH | Sample Ref. | Ph Aft. Ag. | 6 rpm | 3 rpm | A.V. cPs | P.V. cPs | Yv Lb/100 ft2 | (ml) |
| Water | 8.3 | 7.3 | Invention Example 2 | 10.9 | 11 | 7 | 48 | 21 | 54 | 34 |
| | | | Natrosol HI-VIS | 10.1 | 12 | 8 | 45 | 19 | 52 | 31 |

TABLE 15-b

Rheology/FL performance of various HEC samples in 36% NaCl Solution

| Fluid System | | | | Final | Fann DR | | Rheology | | | Fluid Loss |
|---|---|---|---|---|---|---|---|---|---|---|
| Brine | Density ppg | Initial pH | Sample Ref. | Ph Aft. Ag. | 6 rpm | 3 rpm | A.V. cPs | P.V. cPs | Yv Lb/100 ft2 | (ml) |
| Saturated Salt (36% NaCl) | 10.0 | 8.1 | Invention Example 2 | 10.4 | 2 | 1 | 18 | 15 | 7 | 13.2 |
| | | | Natrosol HI-VIS | 10.2 | 11 | 7 | 55 | 26 | 58 | 31.2 |

TABLE 15-c

Rheology/FL performance of various HEC samples in CaBr2 Brine

| Fluid system | | | | Final | Fann DR | | Rheology | | | Fluid Loss |
|---|---|---|---|---|---|---|---|---|---|---|
| Brine | Density ppg | Initial pH | Sample Ref. | PH Aft. Ag. | 6 rpm | 3 rpm | A.V. cPs | P.v. cPs | Yv Lb/100 ft$^2$ | (ml) |
| CaBr2 | 14.5 | 7.43 | Invention Example 2 | 7.5 | 48 | 34 | 132 | 60 | 145 | 29 |
| Did not fully go into solution | | | Natrosol HI-VIS | 7.7 | 7 | 4.4 | 49 | 32 | 33 | Blowout |

TABLE 15-d

Rheology/FL performance of various HEC samples in ZnBr2/CaBr2 brine

| Fluid system | | | | Final | Fann DR | | Rheology | | | Fluid Loss |
|---|---|---|---|---|---|---|---|---|---|---|
| Brine | Density Ppg | Initial pH | Sample Ref. | PH Aft. Ag. | 6 rpm | 3 rpm | A.V. cPs | P.V. cPs | YV lb/100 ft2 | (ml) |
| ZnBr2/CaBr2 | 19.2 | 0.79 | Invention Example 2 | 1.4 | 84 | 68 | Out of Scale | | | 167 |
| | | | Natrosol HI-VIS | 1.23 | | | Did not go into solution | | | |

EXAMPLE 33

Pharmaceuticals

Blocky HEC excipients provide superior tablet hardness. HEC is used in the pharmaceutical industry as an excipient to provide a swellable diffusion barrier in controlled release applications. The gel matrix it forms limits the diffusion of aqueous fluids into a system and dissolved actives out of the system. Currently, HEC produced by Aqualon (Natrosol® 250 series of pharmaceutical grade polymers) holds the majority share of HEC used in the pharmaceutical industry.

HEC has some unique modified release properties not duplicated by hydroxypropylmethyl cellulose (HPMC) and hydroxypropyl cellulose (HPC). However, current knowledge is that current commercial grades of HEC show significantly inferior compression properties when compared to HPMC and HPC. The poor compactibility of this polymer generally makes the polymer suitable for only wet granulation processing, rather than direct compression processing which is frequently the industry preference.

In order to improve this limitation, scientists at Astra Zeneca in International Patent Application, WO 02/19990 A1 describe a procedure whereby HEC is purified by dissolution in water before precipitation via addition of organic solvent. The precipitate is washed and then milled in a specific manner. The purified HEC has markedly improved tablet compactibility.

In accordance with the present invention is the use of blocky HEC material that is highly compressible for making direct compressible tablets for use in compaction applications such as sustained release tablets for pharmaceutical, household, and agricultural applications.

Table 16 shows the strength of pure polymer tablets (with 1% stearic acid for lubrication) made from regular HEC, blocky HEC and commercial Natrosol 250 HHX Pharm HEC. Blocky hydroxyethylcellulose with HE-MS 1.7 achieves a 7-fold increase in tablet hardness as compared to regular Natrosol 250 HHX Pharm. The highly substituted blocky HEC (HE-MS 3.0) achieves a remarkable 12-fold increase in tablet strength. In the typical modified release formulation, these materials all showed excellent direct compression performance and drug release kinetics as compared to commercial Natrosol 250 HHX Pharm.

The data suggest that regions of unsubstituted cellulose backbone appear to be critical for improved HEC compactibility. In the case of the highly substituted, blocky HEC Example 19, the highly substituted ethylene oxide regions may act as a plasticizer resulting in extremely ductile material that is resistant to fracture.

While this invention has been described with respect to specific embodiments, it should be understood that these embodiments are not intended to be limiting and that many variations and modifications are possible without departing from the scope and spirit of this invention.

What is claimed:

1. A composition comprising a hydroxyethylcellulose having hydroxyethyl groups that are non-uniformly distributed on the cellulose backbone, wherein the hydroxyethylcellulose has an unsubstituted trimer ratio (U3R) greater than 0.21 and a hydroxyethyl molar substitution in a range of about 1.3 to about 5.0, wherein the hydroxyethylcellulose composition is produced by the method comprising the steps of:
   A) mixing and reacting a cellulose, water, and a base reagent in an organic solvent to form a first base reagent cellulose mixture, wherein the molar ratio of water to anhydroglucose (AGU) is in a range of about 5 to 35, and wherein either (a) the molar ratio of base reagent to AGU is greater than 1.6, or (b) the molar ratio of base reagent to AGU is less than 0.4:
   B) (i) when (a) is used from Step A, an amount of an acid is then added to reduce the base reagent concentration so that the molar ratio of base reagent to AGU is greater than or equal to 0.6, thereby forming a second base reagent cellulose mixture, or
   (ii) when (b) is used from Step A, an amount of ethylene oxide is then added and reacted to form an intermediate hydroxyethylcellulose product with a hydroxyethyl molar substitution of less than 1.3, followed by additional base reagent to adjust the molar ratio of base reagent to AGU to be greater than 1.0 to form a base reagent hydroxyethylcellulose mixture: and
   C) adding to the second base reagent cellulose mixture from B(i) or to the base reagent hydroxyethylcellulose mixture from B(ii) an amount of ethylene oxide and reacting to form the final hydroxyethylcellulose composition.

2. The composition of claim 1, wherein the unsubstituted trimer ratio (U3R) is greater than 0.235.

3. The composition of claim 1, wherein the hydroxyethyl molar substitution is greater than 1.3 and less than 4.0.

4. A slurry process for making the hydroxyethylcellulose composition of claim 1 comprising the steps of:
   A) mixing and reacting a cellulose, water and a base reagent in an organic solvent to form a first base reagent cellulose mixture, wherein the molar ratio of water to anhydroglucose (AGU) is in a range of about 5 to 35, and wherein either (a) the molar ratio of base reagent to AGU is greater than 1.6, or (b) the molar ratio of base reagent to AGU is less than 0.4,

TABLE 16

Hardness of 99 wt % HEC with 1 wt % Stearic Acid Tablets

| Designation | Process | HE-MS | 1 wt % Solution Viscosity (cps) | Mean Particle Diameter (um) | Tablet Hardness (kP) |
|---|---|---|---|---|---|
| Invention Example 5 | C | 1.7 | 14,400 | 108 | 23.3 |
| Counter Example 5C | A | 1.6 | 1,860 | 105 | 3.0 |
| Natrosol 250 HHX | Commercial | 2.4 | 3,950 | 105 | 2.7 |
| Invention Example 19 | B | 2.9 | 2,640 | 108 | 47.3+ |
| Counter Example 19C | A | 3.0 | 2,980 | 86 | 4.0 |

B) (i) when (a) is used from Step A, an amount of an acid is then added to reduce the base reagent concentration so that the molar ratio of base reagent to AGU is greater than or equal to 0.6, thereby forming a second base reagent cellulose mixture, or (ii) when (b) is used from Step A, an amount of ethylene oxide is then added and reacted to form an intermediate hydroxyethylcellulose product with a hydroxyethyl molar substitution of less than 1.3, followed by additional base reagent to adjust the molar ratio of base reagent to AGU to be greater than 1.0 to form a base reagent hydroxyethylcellulose mixture, and C) adding to the second base reagent cellulose mixture from B(i) or to the base reagent hydroxyethylcellulose mixture from B(ii) an amount of ethylene oxide and reacting to form the final hydroxyethylcellulose composition.

5. The slurry process of claim 4, wherein the organic solvent is selected from the group consisting of ethanol, isopropanol, tert-butanol, acetone, methyl ethyl ketone, and dimethoxyethane and mixtures thereof.

6. The slurry process of claim 4, wherein the base is an alkali selected from the group consisting of lithium hydroxide, sodium hydroxide, potassium hydroxide, and mixtures thereof.

7. The slurry process of claim 4, wherein the cellulose is selected from the group consisting of cotton linters, wood pulps, and mixtures thereof.

8. The slurry process of claim 4, wherein the hydroxyethylcellulose composition of claim 1 is further reacted with at least one other derivatizing reagent to form a modified hydroxyethylcellulose composition.

9. The slurry process of claim 8, wherein the derivatizing reagent is selected from the group consisting of nonionic, cationic, anionic organic compounds and mixtures thereof.

10. The slurry process of claim 9, wherein the organic compounds are selected from the group consisting of halides, epoxides, glycidyl ethers, carboxylic acids, isocyanates, and mixtures thereof.

11. The slurry process of claim 4 or 8, wherein the hydroxyethylcellulose of claim 1 or modified hydroxyethylcellulose composition is further reacted with a viscosity reducing agent.

12. The slurry process of claim 11, wherein the viscosity reducing agent is selected from the group consisting of peroxides, persulfates, peracids, cellulolytic enzymes, salts of halide oxo acids, oxygen, ozone, and combinations thereof.

13. A composition comprising a) a functional system selected from the group consisting of a personal care composition, a household care composition, a pharmaceutical composition, a building and construction composition, an emulsion polymerization composition, an oil field servicing fluid composition, a civil engineering servicing fluid composition, a paper coating composition, a paper making composition, an architectural coating composition, an industrial coating composition, a printing ink composition, an adhesive composition, a mineral processing and recovery composition, and combinations thereof, and b) the hydroxyethylcellulose of claim 1.

14. The composition of claim 13, wherein the functional system is the architectural or industrial coating composition.

15. The coating composition of claim 14, wherein the composition further comprises a binder selected from the group consisting of a latex, an alkyd resin, a urethane resin, a silicone resin, an epoxy resin, and combinations thereof.

16. The composition of claim 13, wherein the functional system is the building and construction material composition selected from the group consisting of concrete, tile cements and adhesives, plasters, stuccos, mortars, underwater concrete, joint compound or cement, crack fillers, floor screeds, adhesive mortars, and combinations thereof.

17. The composition of claim 16, wherein the building and construction material composition is a joint compound or cement.

18. The composition of claim 17, wherein the joint compound or cement contains less than 0.5% clay.

19. The composition of claim 13, wherein the functional system is the personal care composition.

20. The composition of claim 19, wherein the personal care composition is selected from the group consisting of skin care, hair care, oral care, nail care, personal hygiene products, and combinations thereof.

21. The composition of claim 13, wherein the functional system is the household care composition.

22. The composition of claim 21, wherein the household care composition is selected from the group consisting of fabric care, laundry detergent, hard surface cleaner, industrial institutional liquid soaps, dish detergents, and combinations thereof.

23. The composition of claim 13, wherein the functional system is the oil field servicing fluid composition.

24. The composition of claim 23, wherein the oil field servicing fluid composition is selected from the group consisting of drilling fluid, completion or workover fluid, fracturing fluids, oil well cementing fluids, and combinations thereof.

25. The composition of claim 13, wherein the functional system is the paper coating composition.

26. The composition of claim 13, wherein the functional system is the paper making composition.

27. The composition of claim 13, wherein the functional system is the pharmaceutical composition.

28. The composition of claim 27, wherein the pharmaceutical composition has a form selected from the group consisting of tablet, capsule, granules, and combinations thereof.

29. The composition of claim 27, wherein the hydroxyethylcellulose of claim 1 is used as an excipient.

30. The composition of claim 1, wherein the hydroxyethylcellulose is modified with one or more substituents having a chemical functionality selected from the group consisting of nonionic, anionic, cationic, and combinations thereof.

31. The composition of claim 30, wherein the substituents are attached to the hydroxyethylcellulose backbone via an ether, ester, or urethane linkage moiety.

32. The composition of claim 30, wherein the substituents have a cationic chemical functionality.

33. The composition of claim 32, wherein the substituents have the formula $R^1R^2R^3R^4N+(A-)$, wherein:

$R^1$ is $-CH_2-CHOH-CH_2-$ or $-CH_2-CH_2-$ $R^2$, $R^3$, $R^4$ are each independently selected from the group consisting of an alkyl and aryl alkyl group having 1 to 20 carbon atoms; and A- is a halide, sulfate, phosphate, or tetrafluoroborate.

34. The composition of claim 33, wherein the substituents are selected from the group consisting of 2-hydroxypropyltrimethylammonium chloride, 2-hydroxypropyldodecyldimethylammonium chloride, 2-hydroxypropylcocoalkyldimethylammonium chloride, 2-hydroxypropyloctadecyldimethylammonium chloride, and combinations thereof.

35. The composition of claim 30, wherein the modified hydroxyethylcellulose is selected from the group consisting of methyl hydroxyethylcellulose, ethyl hydroxyethylcellulose, octyl hydroxyethylcellulose, cetyl hydroxyethylcellulose, cetoxy-2-hydroxypropyl hydroxyethylcellulose, butoxy-2-hydroxypropyl hydroxyethylcellulose, butoxy-2-hydroxypropyl cetyl hydroxyethylcellulose, butoxy-2-hydroxypropyl cetoxy-2-hydroxyethylcellulose, carboxymethyl hydroxyethylcellulose, carboxymethyl ethyl hydroxyethylcellulose, carboxymethyl octyl hydroxyethylcellulose, carboxymethyl cetyl hydroxyethylcellulose, carboxymethyl cetoxy-2-hydroxypropylcellulose, carboxymethyl butoxy-2-hydroxyethylcellulose, sulfoethyl hydroxyethylcellulose, sulfoethyl ethyl hydroxyethylcellulose, sulfoethyl cetyl hydroxyethylcellulose, sulfoethyl cetoxy-2-hydroxypropylcellulose, 2-hydroxpropyltrimethylammonium chloride hydroxyethylcellulose, 2-hyroxypropyltrimethylammonium chloride ethyl hydroxyethylcellulose, 2-hydroxypropyltrimethylammonium chloride butoxy-2-hydroxypropyl hydroxyethylcellulose, 2-hydroxypropyltrimethylammonium chloride octyl hydroxyethylcellulose, 2-hydroxypropyltrimethylammonium chloride cetyl hydroxyethylcellulose, 2-hydroxypropyltrimethylammonium chloride cetoxy-2-hydroxypropyl hydroxyethylcellulose, 2-hydroxypropyllauryldimethylammonium chloride hydroxyethylcellulose, 2-hydroxypropyltrimethylammonium chloride 2-hydroxypropyllauryldimethylammonium chloride hydroxyethylcellulose, diallyldimethylammonium chloride hydroxyethylcellulose graft copolymer, diallyldimethylammoniumchloride cetyl hydroxyethylcellulose graft copolymer, and combinations thereof.

* * * * *